(12) United States Patent  (10) Patent No.: US 8,492,508 B2
Liaw  (45) Date of Patent: Jul. 23, 2013

(54) NITRO COMPOUND, AMINE COMPOUND, POLYIMIDE AND POLYIMIDE COPOLYMER DERIVED THEREFROM

(75) Inventor: Der-Jang Liaw, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 144 days.

(21) Appl. No.: 12/925,497

(22) Filed: Oct. 22, 2010

(65) Prior Publication Data

US 2011/0275781 A1 Nov. 10, 2011

(30) Foreign Application Priority Data

May 4, 2010 (TW) .............................. 99114190 A

(51) Int. Cl.
C08G 69/26 (2006.01)
(52) U.S. Cl.
USPC ............ 528/342; 567/157; 564/306; 564/326
(58) Field of Classification Search
USPC ..................... 528/342; 567/157; 564/306, 326
See application file for complete search history.

(56) References Cited

PUBLICATIONS

Chang et al. (Polymer, 51, 2010, 4493-4502, P/D Aug. 3, 2010).*

* cited by examiner

*Primary Examiner* — Shane Fang
(74) *Attorney, Agent, or Firm* — J.C. Patents

(57) ABSTRACT

A polyimide represented by formula (6) is provided. The polyimide is fabricated by performing a polycondensation reaction with a amine compound shown in formula (4) and a dianhydride compound shown in formula (5) as monomers. In formulas (5) and (6), Ar represents aromatic group, and n represents a positive integer.

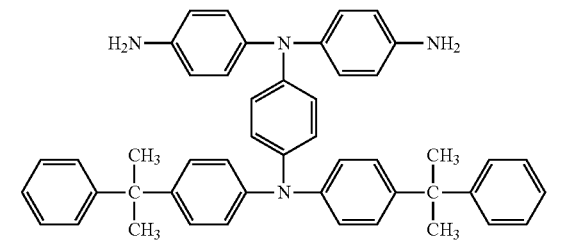

Formula (4)

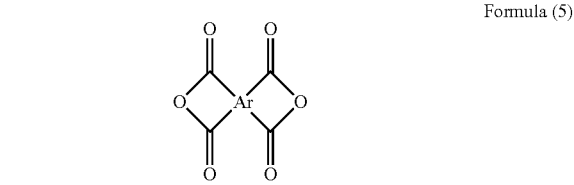

Formula (5)

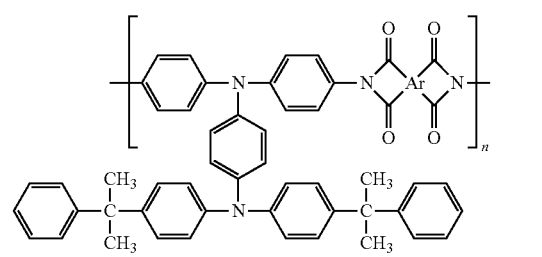

Formula (6)

6 Claims, 14 Drawing Sheets
(3 of 14 Drawing Sheet(s) Filed in Color)

NITRO COMPOUND, AMINE COMPOUND, POLYIMIDE AND POLYIMIDE COPOLYMER DERIVED THEREFROM

CROSS-REFERENCE TO RELATED APPLICATION

This application claims the priority benefit of Taiwan application serial no. 99114190, filed on May 4, 2010. The entirety of the above-mentioned patent application is hereby incorporated by reference herein and made a part of this specification.

BACKGROUND OF THE INVENTION

1. Field of the Invention

The invention relates to a nitro compound, an amine compound, a polyimide, and a polyimide copolymer. More particularly, the invention relates to a new nitrophenyl compound containing a triphenylamide group, a new phenylamine compound fabricated with the nitrophenyl compound, a new dinitro compound fabricated with the phenylamine compound, a new diamine compound fabricated with the dinitro compound, a new polyimide and a new polyimide copolymer fabricated with the aforementioned diamine compound and at least one dianhydride compound.

2. Description of Related Art

Polyimide (PI) is currently one of the most important engineering plastics. With the features of superior thermal stability, resistance to chemical reagents, low dielectric constant, abrasion resistance, low thermal expansion coefficient and other properties, PI is a good candidate to be widely applied as electronic material in relevant electronic industries such as automobile industry, semiconductor industry, precision machinery industry, soft printed circuit board, liquid crystal display (LCD), and other electronics industries.

Although PI has superior heat-resistance and mechanical characteristics, the problem of unfavorable processability is usually present. Moreover, PI has high melting point or softening point and therefore can not be processed by heating and melting. Also, PI has low solubility, and thus can not be processed to form by dissolving with a solvent. Hence, most of aromatic PIs have difficulties in the formation processing.

Some patents disclosed that the rigidness of molecular chain is reduced by introducing soft fats, such as a straight alkyl group ($-CH_2-$), into the structure, so as to enhance solubility of polymer. However, the heat-resistance of polymer is usually reduced at the same time.

SUMMARY OF THE INVENTION

Accordingly, the invention is directed to a nitro compound, an amine compound, a polyimide (PI) and a PI copolymer derived therefrom. The foregoing polymers contain triphenylamide and therefore have superior solubility, high glass transition temperature, high thermal stability, and have electrochemical properties and electrochromic properties.

A nitro compound is provided in the invention. The nitro compound is a nitrophenyl compound of 4,4'-di-isopropylphenyl-4''-nitrotriphenyl-amine (DIPNTPA) represented by Formula (1).

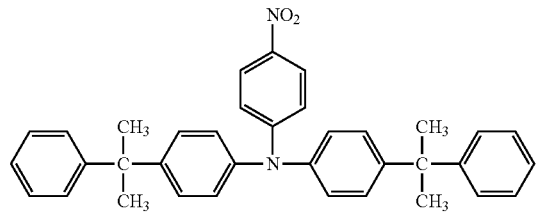

Formula (1)

An amine compound is provided in the invention. The amine compound is a phenylamine compound of 4-amino-4', 4''-di-isopropylphenyl-triphenylamine (ADIPTPA), fabricated by using the nitro compound represented in Formula (1) as a monomer. The amine compound is represented by Formula (2).

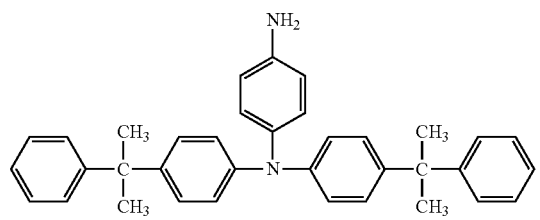

Formula (2)

A nitro compound is provided in the invention. The nitro compound is a dinitro compound of N,N-bis(4-diisopropylphenyl)-N',N'-bis(4-nitrophenyl)-1,4-phenylenediamine (BDBNPD), fabricated by using the amine compound represented in Formula (2) as a monomer. The nitro compound is represented by Formula (3).

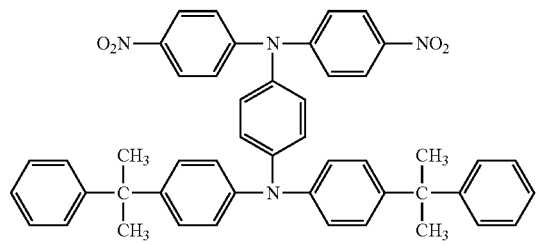

Formula (3)

An amine compound is provided in the invention. The amine compound is a diamine compound of N,N-bis(4-aminophenyl)-N',N'-bis(4-diisopropylphenyl)-1,4-phenylenediamine (BABDPD), fabricated by using the nitro compound represented in Formula (3) as a monomer. The amine compound is represented by Formula (4).

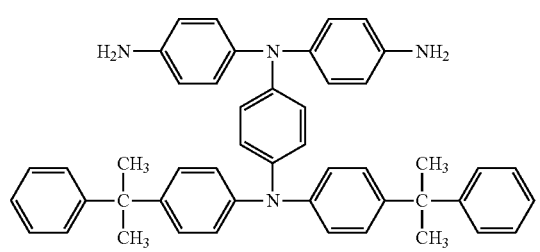

Formula (4)

A PI is provided in the invention. The PI is fabricated by performing a polycondensation reaction with the amine compound represented by Formula (4) and a dianhydride compound represented by Formula (5) as monomers. The PI is represented by Formula (6):

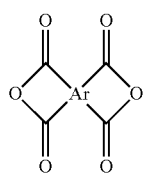

Formula (5)

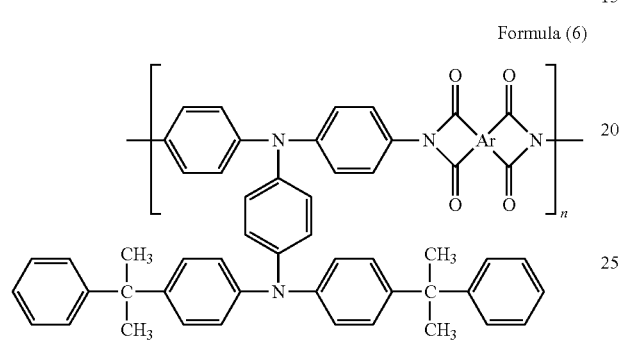

Formula (6)

where in Formulae (5) and (6), Ar represents an aromatic group, and n represents a positive integer.

According to an embodiment of the invention, in Formulae (5) and (6), Ar represents a group selected from Formulae (5-1) to (5-6).

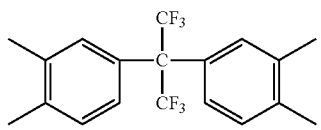

Formula (5-1)

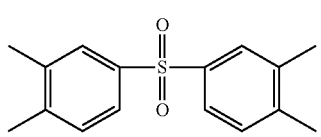

Formula (5-2)

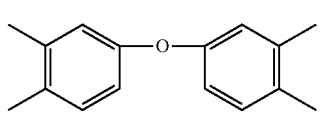

Formula (5-3)

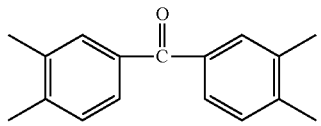

Formula (5-4)

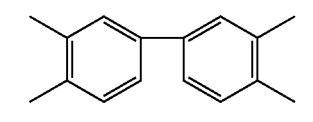

Formula (5-5)

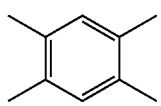

Formula (5-6)

A PI copolymer is provided in the invention. The PI copolymer is fabricated by performing a copolymerization reaction with different molar ratios of the amine compound represented by Formula (4) and at least one dianhydride compound shown in Formula (5) as monomers:

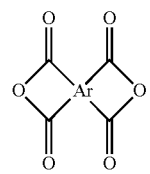

Formula (5)

where in Formula (5), Ar represents an aromatic group.

According to an embodiment of the invention, in Formulae (5) and (6), Ar represents a group selected from Formulae (5-1) to (5-6).

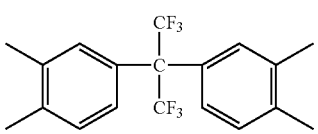

Formula (5-1)

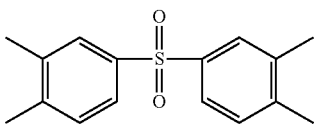

Formula (5-2)

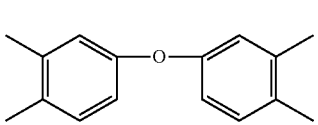

Formula (5-3)

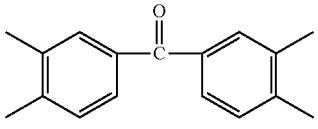

Formula (5-4)

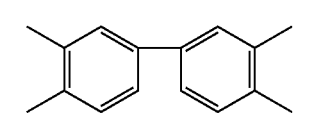

Formula (5-5)

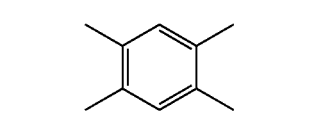

Formula (5-6)

According to an embodiment of the invention, the at least one dianhydride compound adopted as monomers includes two different dianhydride compounds, and the polyimide copolymer can be represented by Formula (7):

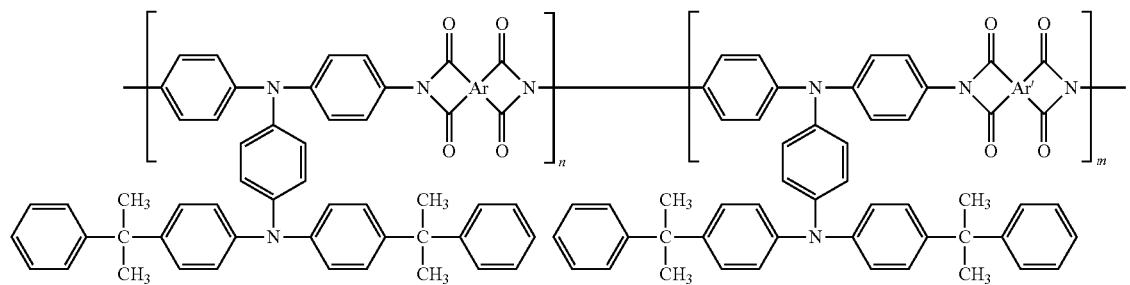

Formula (7)

where in Formula (7), Ar and Ar' respectively represent aromatic groups that are different from each other, and m and n respectively represent positive integers.

According to an embodiment of the invention, in Formula (7), Ar and Ar' respectively represent two groups selected from Formula (5-1) to Formula (5-6).

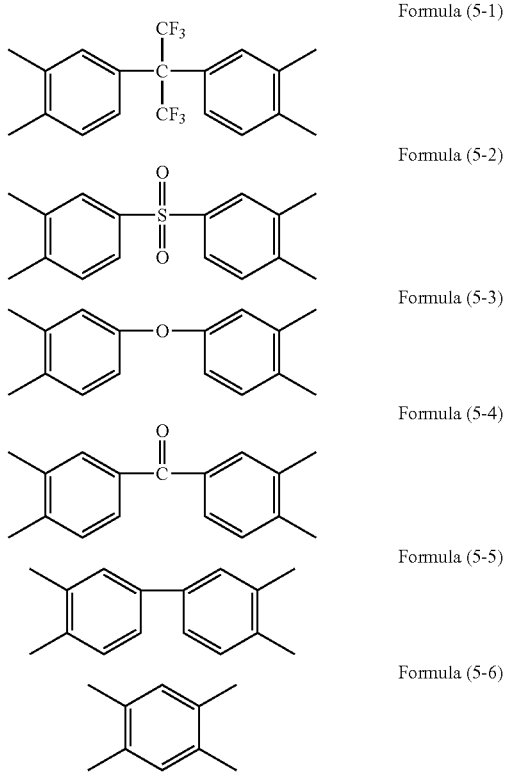

Formula (5-1)
Formula (5-2)
Formula (5-3)
Formula (5-4)
Formula (5-5)
Formula (5-6)

In light of the foregoing, the technical feature of the invention includes a new nitrophenyl compound containing a triphenylamide group, a new phenylamine compound fabricated with the nitrophenyl compound, a new dinitro compound fabricated with the phenylamine compound, a new diamine compound fabricated with the dinitro compound, and a new PI and a PI copolymer fabricated with the aforementioned diamine compound and the at least one dianhydride compound. The new PI and new PI copolymer contain a bistriphenylamide group and thus have superior solubility, high glass transition temperature and high thermal stability. Consequently, the processability of PI can be improved to enhance the application thereof. Furthermore, the new PI and new PI copolymer also have electrochemical properties and electrochromic properties.

In order to make the aforementioned and other features and advantages of the invention more comprehensible, several embodiments accompanied with figures are described in detail below.

BRIEF DESCRIPTION OF THE DRAWINGS

The patent or application file contains at least one drawing executed in color. Copies of this patent or patent application publication with color drawings will be provided by the Office upon request and payment of the necessary fee. The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

In the following, the technical features of the invention including a new nitrophenyl compound containing a triphenylamide group, a new phenylamine compound fabricated with the nitrophenyl compound, a new dinitro compound fabricated with the phenylamine compound, a new diamine compound fabricated with the dinitro compound, and a new polyimide and a new polyimide copolymer fabricated with the aforementioned diamine and at least one dianhydride compound are provided.

I. Nitrophenyl Compound

A nitro compound of an embodiment of the invention is a nitrophenyl compound of 4,4'-di-isopropylphenyl-4"-nitrotriphenylamine (DIPNTPA), as illustrated in Formula (1). Moreover, DIPNTPA contains triphenylamide.

Formula (1)

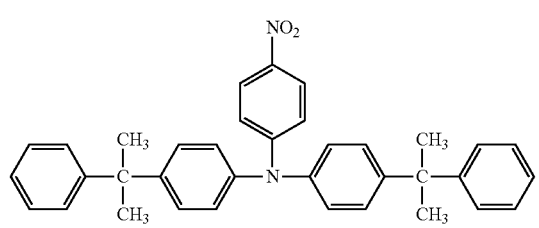

Thereafter, a method of synthesizing DIPNTPA is illustrated with an example. The chemical structure of a compound fabricated is further identified and analyzed.

Firstly, 49 milli-mole (mmole) of bis[4-(2-phenyl-2-propyl)phenylamine], 49 mmole of 1-fluoro-4-nitrobenzene, 49 mmole of sodium hydride, and 120 milli-liter (ml) of dimethyl sulfoxide are placed in a reaction vessel and reacted for 48 hours at 120° C. to obtain a reaction mixture. Next, the cooled reaction mixture is precipitated in methanol to obtain the solid portion. Afterwards, a yellow solid, that is, DIPNTPA, is obtained from the solid portion by column chromatography with a solvent ratio of n-hexane:dichloromethane=2:1. DIPNTPA has a measured melting point of 150-151° C. and a production yield of 50%.

A synthetic reaction of DIPNTPA aforementioned is shown in the following.

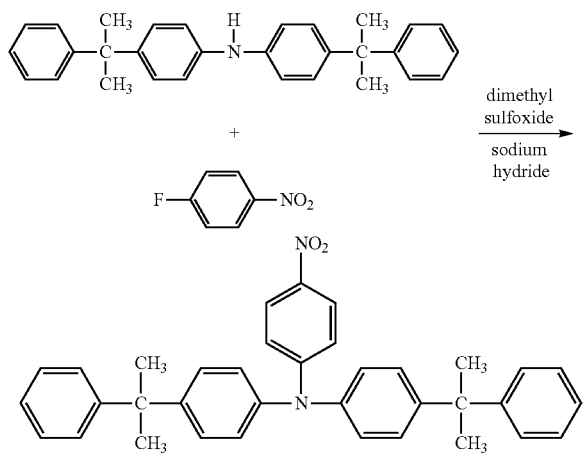

Figure 1:
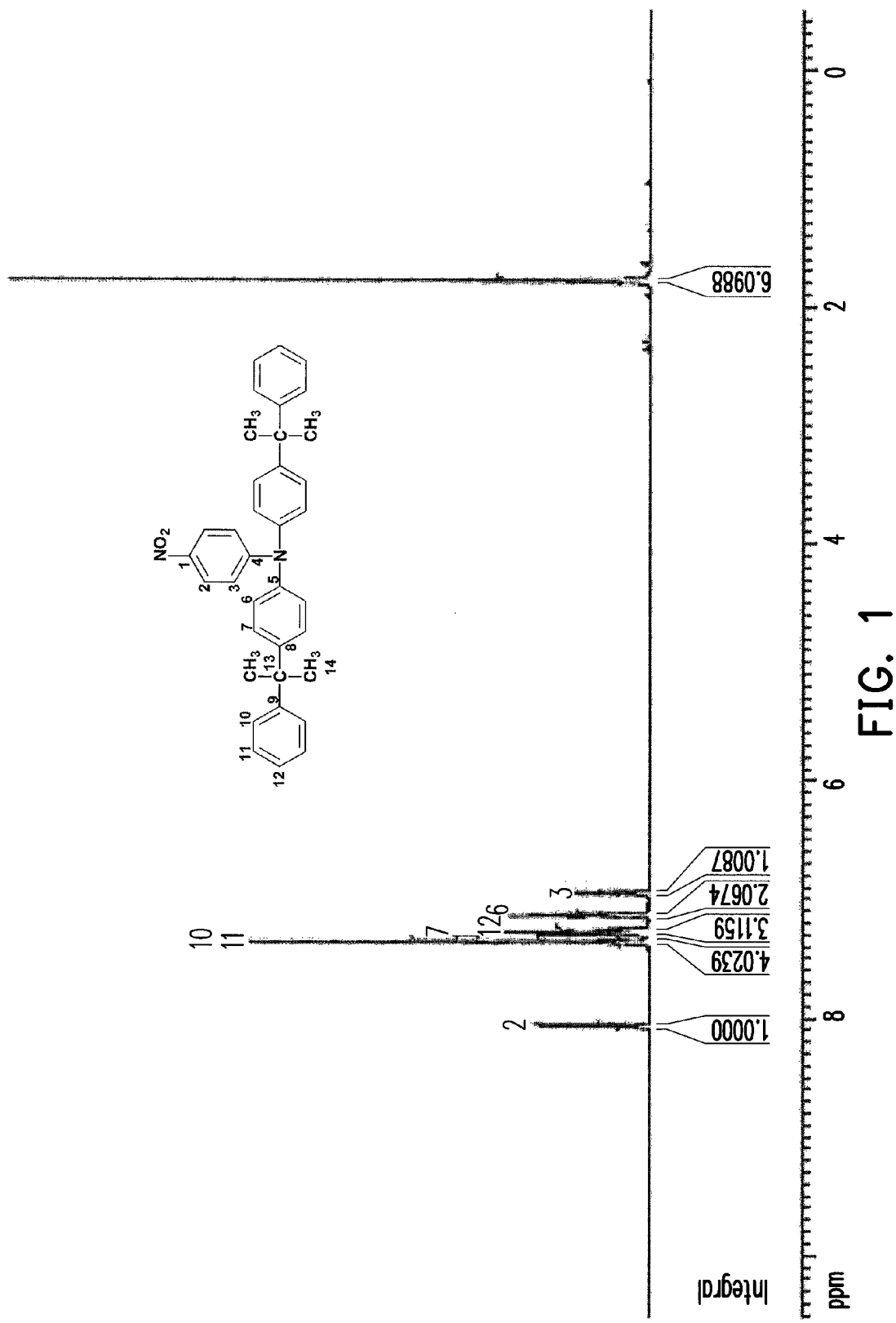
FIGS. 1 and 2 respectively illustrate schematic nuclear magnetic resonance (NMR) spectrums of $^1$H-NMR and $^{13}$C-NMR of a DIPNTPA nitrophenyl compound according to an embodiment of the invention.
Figure 2:
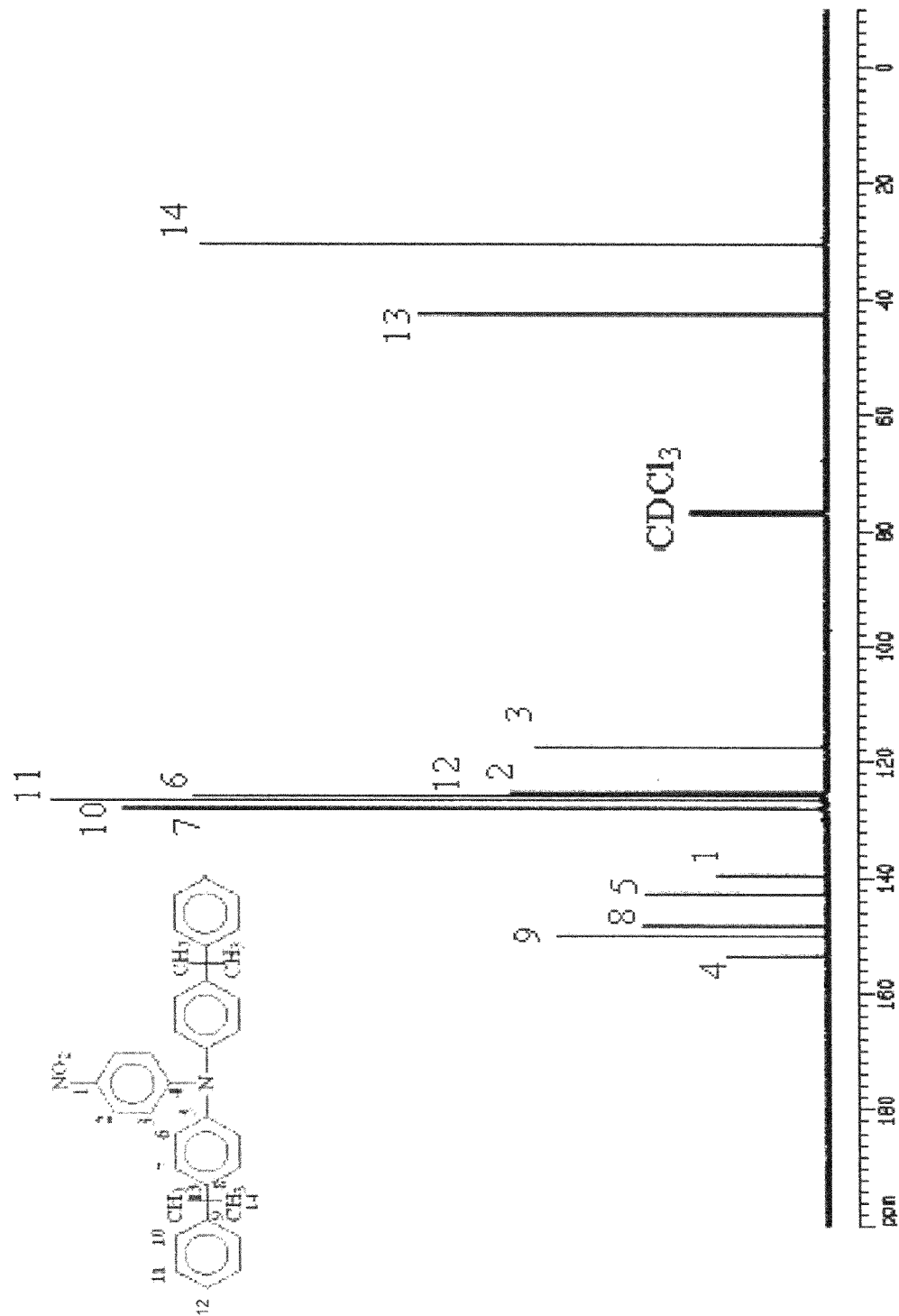

In addition, DIPNTPA obtained is identified by using a $^1$H-NMR analysis and a $^{13}$C-NMR analysis of a nuclear magnetic resonance spectrum (NMR spectrum) and an element analysis. FIGS. 1 and 2 respectively illustrate schematic NMR spectrums of $^1$H-NMR and $^{13}$C-NMR of a DIPNTPA nitrophenyl compound according to an embodiment of the invention. In the NMR spectrums shown in FIGS. 1 and 2, s represents a singlet, d represents a doublet, t represents a triplet, q represents a quartet, and m represents a multiplet.

$^1$H NMR (CDCl$_3$): δ(ppm)=8.05-8.08 (d, 1H); 7.37-7.38 (d, 2H); 7.35-7.36 (t, 2H); 7.28-7.30 (d, 2H); 7.24-7.27 (m, 1H); 7.12-7.14 (d, 2H); 6.93-6.95 (d, 1H); 1.78 (s, 6H).

$^{13}$C NMR (CDCl$_3$): δ(ppm)=153.46, 150.01, 148.26, 142.80, 139.62, 128.13, 128.03, 126.62, 125.88, 125.71, 125.31, 117.42, 42.62, 30.65.

The element analysis result of the DIPNTPA nitrophenyl compound of the present embodiment is presented below. Theoretical values are: C, 82.10%; H, 6.51%; N, 5.32%. Analytical values are: C, 81.67%; H, 6.39%; N, 5.21%.

II. Phenylamine Compound

An amine compound of an embodiment of the invention is a phenylamine compound of 4-amino-4',4"-di-isopropylphenyl-triphenylamine (ADIPTPA), as illustrated in Formula (2). Moreover, ADIPTPA contains triphenylamide.

Formula (2)

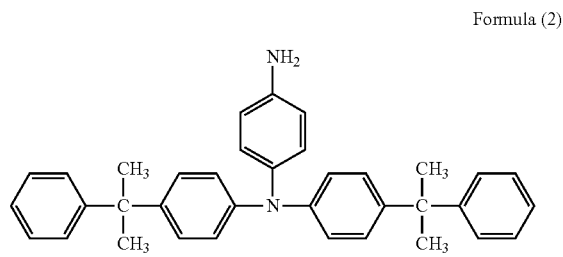 [SMILES: CC(C)(c1ccccc1)c1ccc(N(c2ccc(N)cc2)c2ccc(C(C)(C)c3ccccc3)cc2)cc1]

Thereafter, a method of synthesizing ADIPTPA is illustrated with an example. The chemical structure of a compound fabricated is further identified and analyzed.

Firstly, 33.46 mmole of DIPNTPA monomer, 0.3 gram (g) of 10% Pd/C, and 200 ml of ethanol are placed in a reaction vessel. The mixture is heated to 90° C., and 10 ml of hydrazine (H$_2$NNH$_2$.H$_2$O) is then slowly added into the mixture. After hydrazine has been added, the mixture is reacted for 24 hours. Upon completion of the reaction, the mixture is filtered while still hot so that the 10% Pd/C is removed and the filtered solution is obtained. After the filter solution obtained is cooled and precipitated, another filtration is performed to obtain the solid portion. The solid obtained is then crystallized twice with ethanol so as to obtain a white amine compound. The white amine compound is dried under a vacuum environment. ADIPTPA has a measured melting point of 107-108° C. and a production yield of 60%.

A synthetic reaction of ADIPTPA aforementioned is shown in the following.

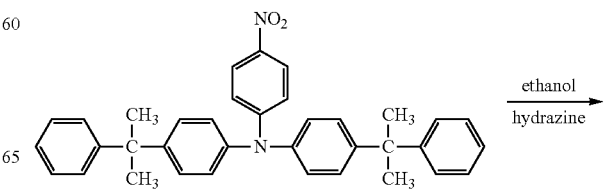

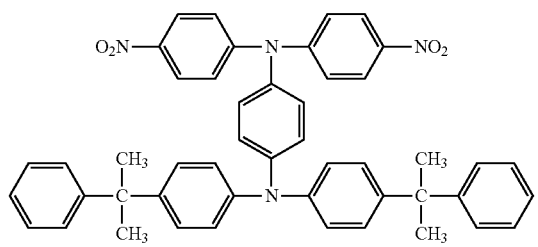

Figure 3:
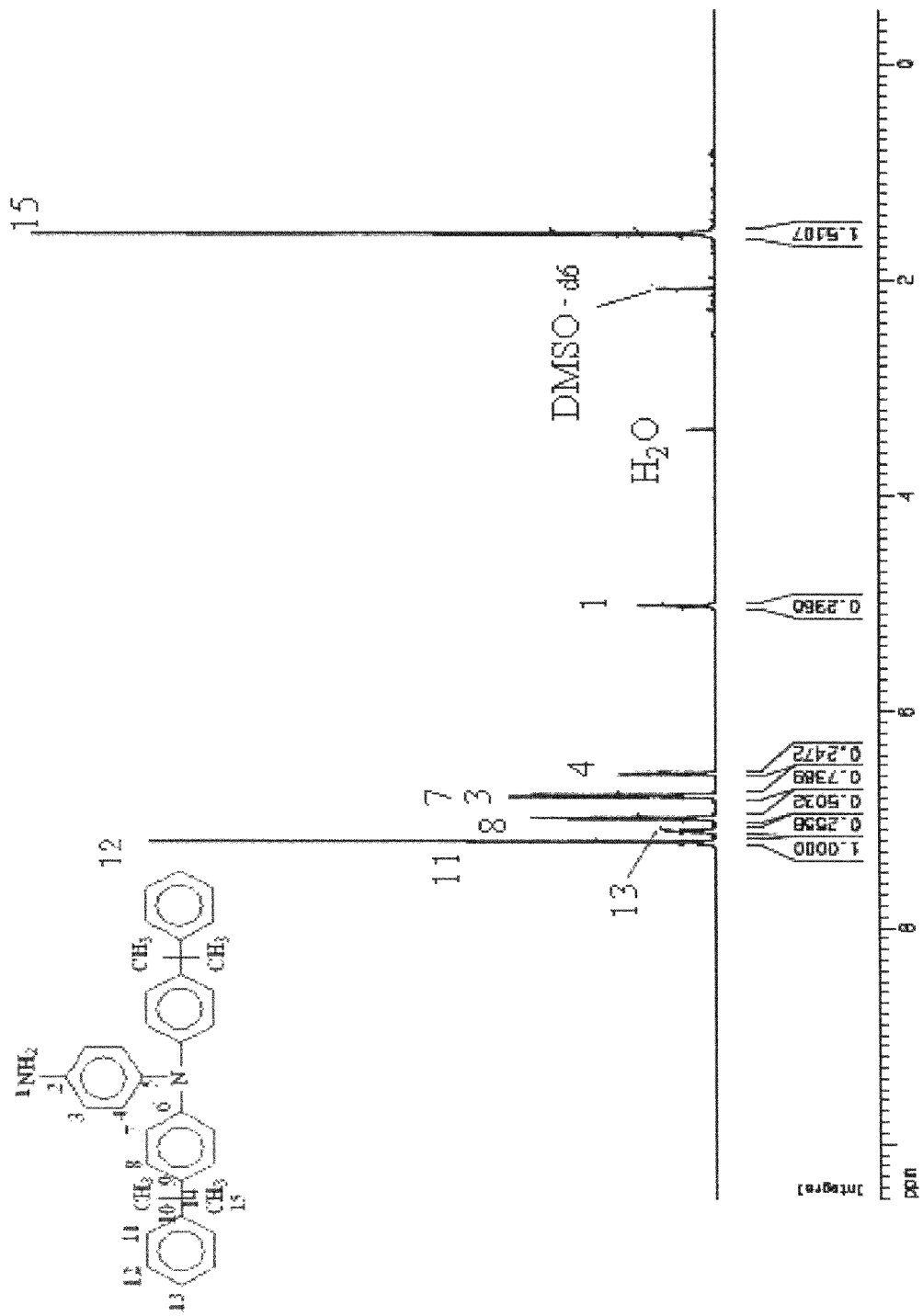
FIGS. 3 and 4 respectively illustrate schematic NMR spectrums of $^1$H-NMR and $^{13}$C-NMR of an ADIPTPA phenylamine compound according to an embodiment of the invention.
Figure 4:
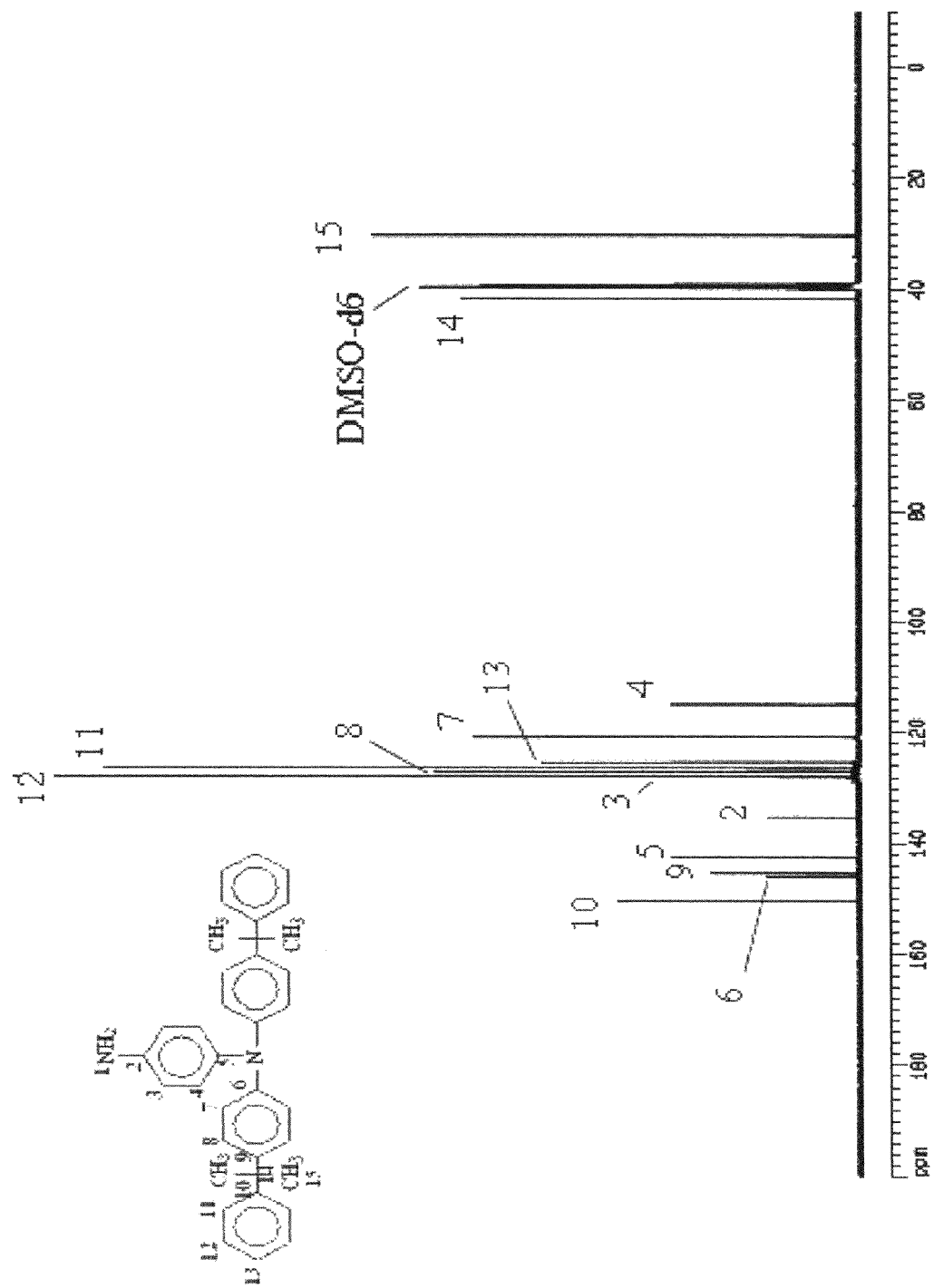

In addition, ADIPTPA obtained is identified using the $^1$H-NMR analysis and the $^{13}$C-NMR analysis of the NMR spectrum and the element analysis. FIGS. 3 and 4 respectively illustrate schematic NMR spectrums of $^1$H-NMR and $^{13}$C-NMR of an ADIPTPA phenylamine compound according to an embodiment of the invention. In the NMR spectrums shown in FIGS. 3 and 4, s represents a singlet, d represents a doublet, t represents a triplet, q represents a quartet, and m represents a multiplet.

$^1$H NMR (DMSO-d$_6$): δ(ppm)=7.20-7.21 (d, 2H); 7.19-7.20 (d, 2H); 7.09-7.12 (m, H); 6.98-7.00 (d, 2H); 6.79 (d, 2H); 6.77 (d, 2H); 6.56-6.58 (d, 1H); 5.02 (s, 1H); 1.57 (s, 6H).

$^{13}$C NMR (DMSO-d$_6$): δ(ppm)=150.3, 145.9, 145.4, 142.5, 135.2, 125.3, 127.9, 127.8, 126.9, 126.2, 125.3, 120.73, 114.9, 41.7, 30.3.

The element analysis result of ADIPTPA of the present embodiment is presented below. Theoretical values are: C, 87.05%; H, 7.31%; N, 5.64%. Analytical values are: C, 86.90%; H, 7.13%; N, 5.61%.

III. Dinitro Compound

A nitro compound of an embodiment of the invention is a dinitro compound of N,N-bis(4-diisopropylphenyl)-N',N'-bis(4-nitrophenyl)-1,4-phenylenediamine (BDBNPD), as illustrated in Formula (3). Moreover, BDBNPD contains bis-triphenylamide.

Formula (3)

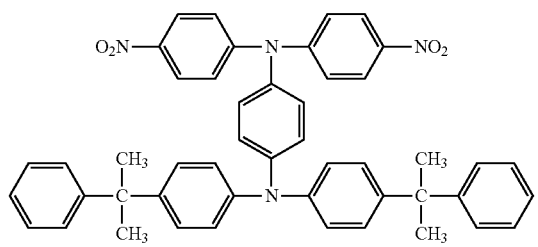

Thereafter, a synthetic method of BDBNPD is illustrated with an example. A chemical structure of a compound fabricated is further identified and analyzed.

Firstly, 14.63 mmole of ADIPTPA, 29.27 mmole of 1-fluoro-4-nitrobenzene, 29.27 mmole of cesium fluoride, and 80 ml of dimethyl sulfoxide are placed in a reaction vessel and reacted for 24 hours at 120° C. The cooled reaction mixture is then precipitated in methanol to obtain the solid portion. Afterwards, a yellow solid, that is, BDBNPD, is obtained from the solid portion by column chromatography with a solvent ratio of n-hexane:dichloromethane=1:1. BDBNPD has a measured melting point of 224-225° C. and a production yield of 50%.

A synthetic reaction of BDBNPD aforementioned is shown in the following.

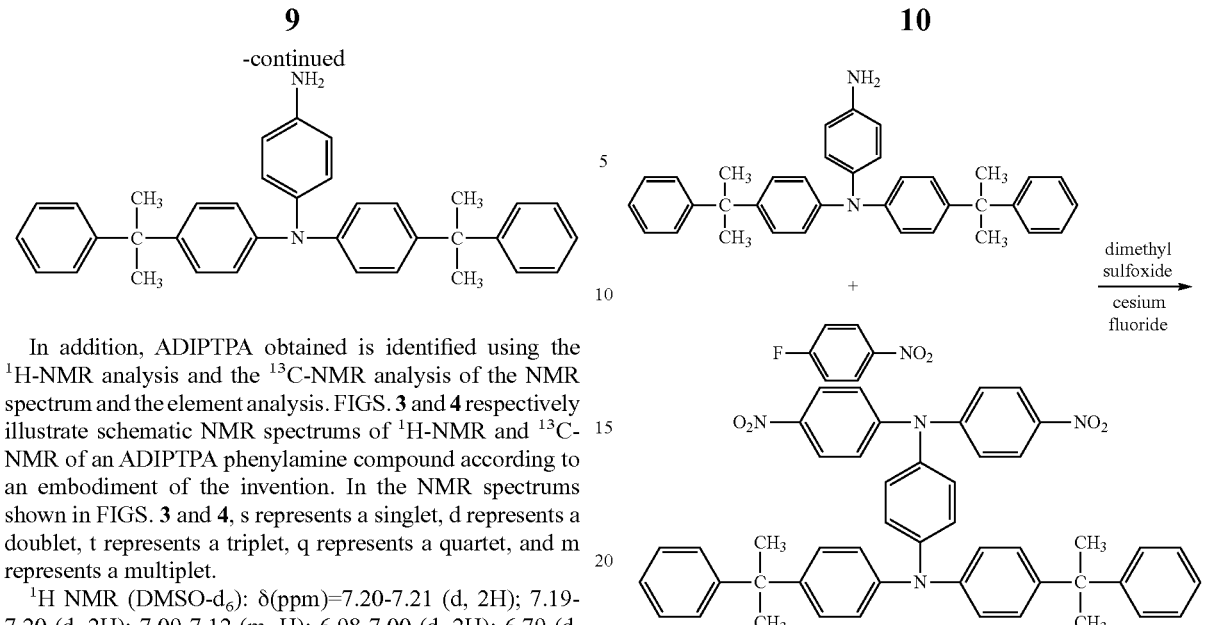

Figure 5:
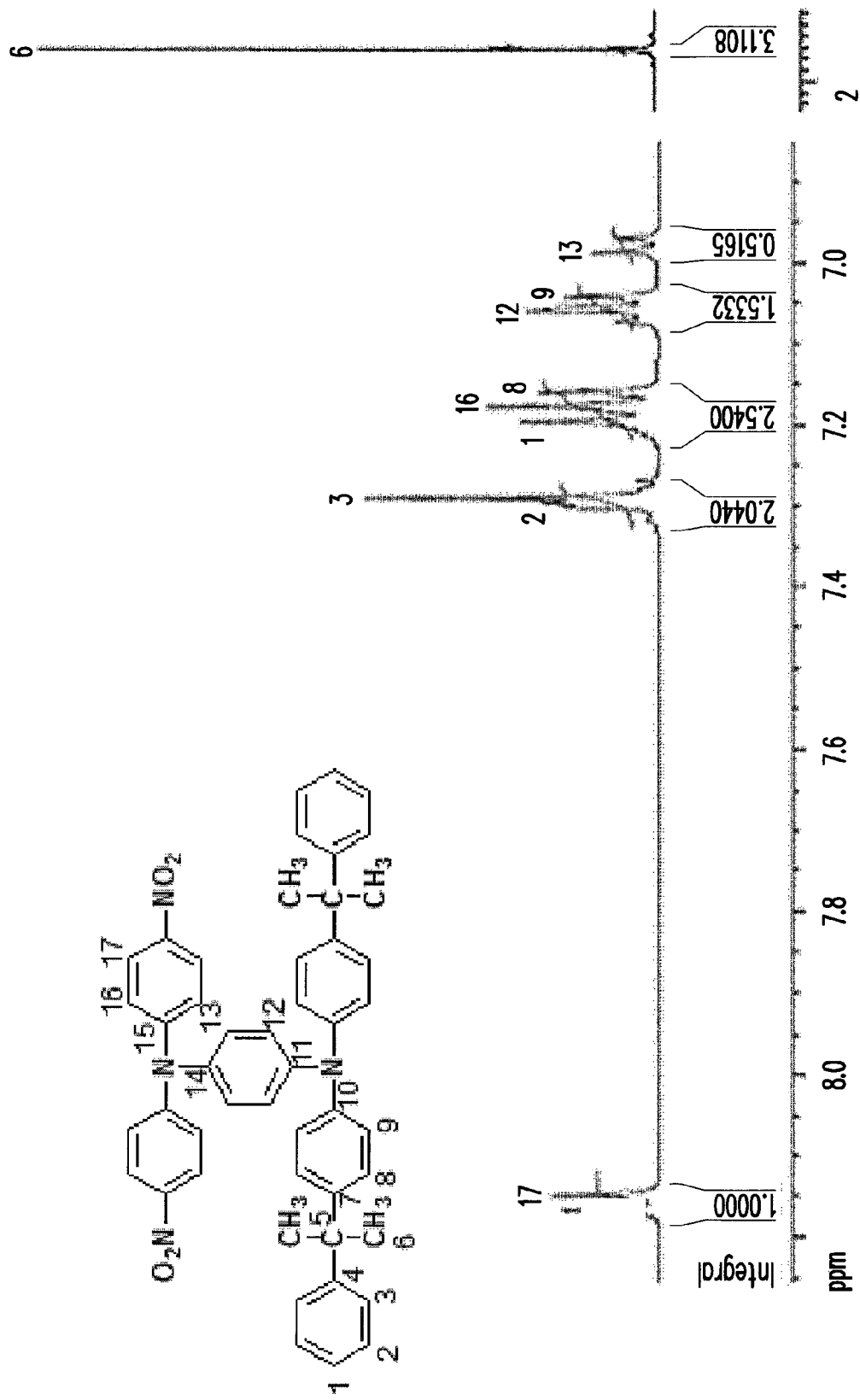
FIGS. 5 and 6 respectively illustrate schematic NMR spectrums of $^1$H-NMR and $^{13}$C-NMR of a BDBNPD dinitro compound according to an embodiment of the invention.
Figure 6:
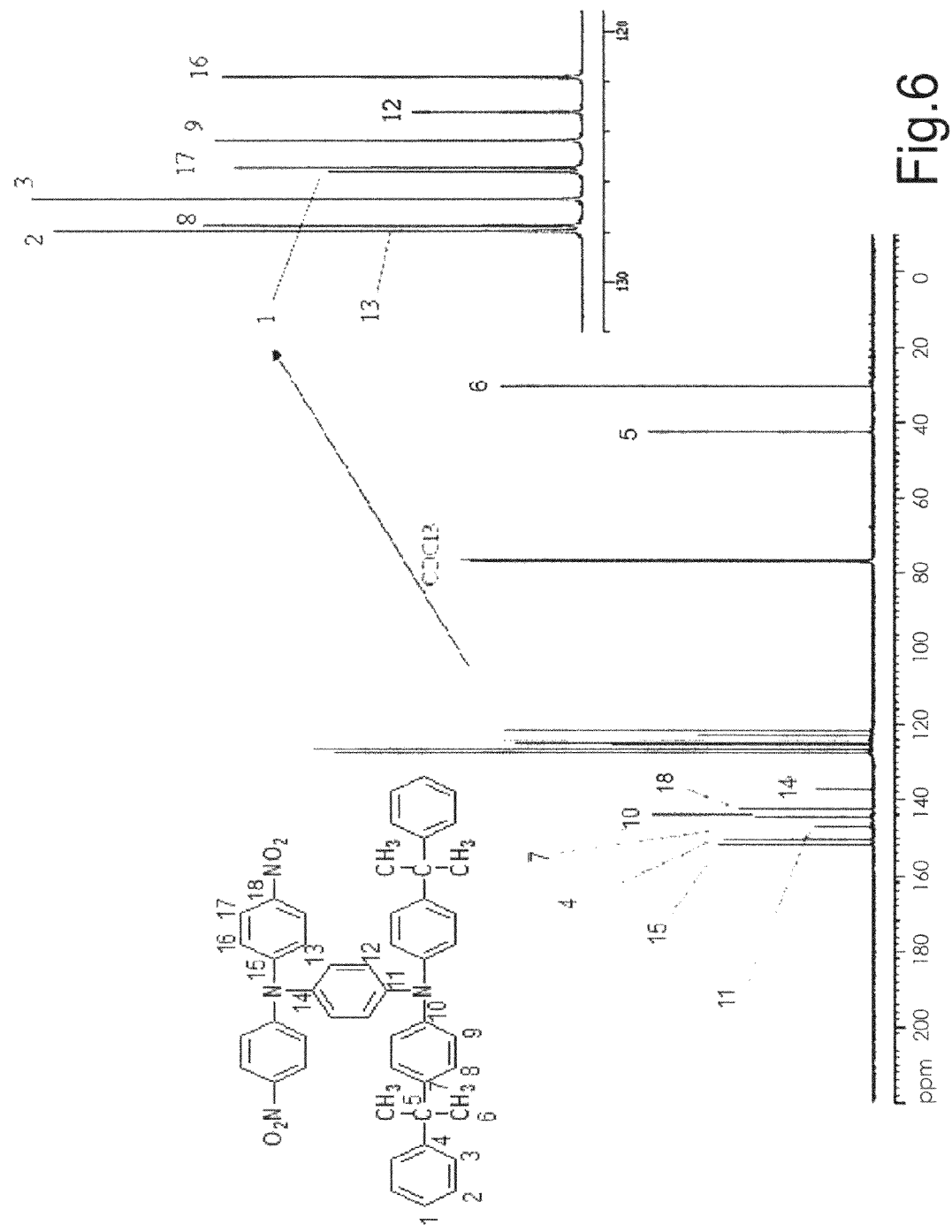

In addition, BDBNPD obtained is identified using the $^1$H-NMR analysis and the $^{13}$C-NMR analysis of the NMR spectrum and the element analysis. FIGS. 5 and 6 respectively illustrate schematic NMR spectrums of $^1$H-NMR and $^{13}$C-NMR of a BDBNPD dinitro compound according to an embodiment of the invention. In the NMR spectrums shown in FIGS. 5 and 6, s represents a singlet, d represents a doublet, t represents a triplet, q represents a quartet, and m represents a multiplet.

$^1$H NMR (CDCl$_3$): δ(ppm)=8.14-8.17 (d, 2H); 7.30-7.31 (t, 2H); 7.28-7.29 (d, 2H); 7.21 (m, 1H); 7.17-7.19 (d, 2H); 7.15-7.17 (d, 2H); 7.05-7.07 (d, 2H); 7.04-7.05 (d, 2H); 6.97-6.98 (d, 2H); 1.70 (s, 6H, Hd).

$^{13}$C NMR (CDCl$_3$): δ(ppm)=151.7, 150.4, 147.0, 146.1, 144.3, 142.3, 137.2, 127.96, 127.94, 127.7, 126.6, 125.6, 125.4, 124.3, 123.2, 121.8, 42.5, 30.7.

The element analysis result of BDBNPD of the present embodiment is presented below. Theoretical values are: C, 78.03%; H, 5.73%; N, 7.58%. Analytical values are: C, 77.57%; H, 5.63%; N, 7.45%.

IV. Diamine Compound

An amine compound of an embodiment of the invention is a diamine compound of N,N-bis(4-aminophenyl)-N',N'-bis(4-diisopropylphenyl)-1,4-phenylenediamine (BABDPD), as illustrated in Formula (4). Moreover, BABDPD contains bis-triphenylamide.

Formula (4)

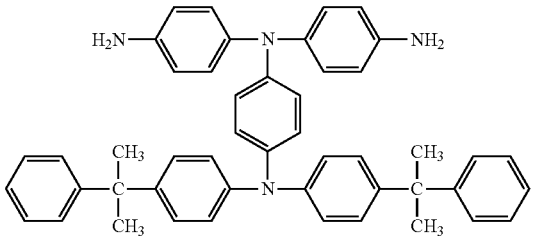

Next, a method of fabricating BABDPD is illustrated with an example. A chemical structure of a compound fabricated is further identified and analyzed.

Firstly, 4.1 mmole of BDBNPD monomer, 0.1 gram of 10% Pd/C, and 120 ml of ethanol are placed in a reaction vessel. The mixture is heated to 90° C., and 3 ml of hydrazine is then slowly added into the mixture. After hydrazine has been added, the mixture is reacted for 24 hours. Upon completion of the reaction, the mixture is filtered while still hot so that the 10% Pd/C is removed and the filtered solution is obtained. After the filter solution obtained is cooled and precipitated, another filtration is performed to obtain the solid portion. A pink diamine compound is obtained from the solid portion by using column chromatography with a solvent ratio of ethyl acetate:n-hexane=1:3. The pink diamine compound is then dried under a vacuum environment. BABDPD has a measured melting point of 200-201° C. and a production yield of 60%.

A synthetic reaction of BABDPD aforementioned is shown in the following.

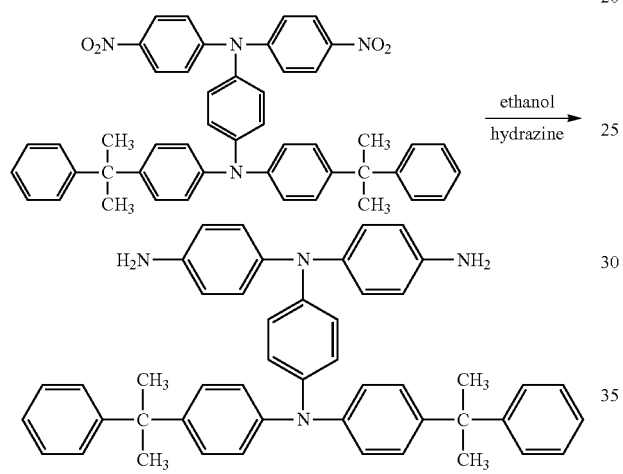

Figure 7:
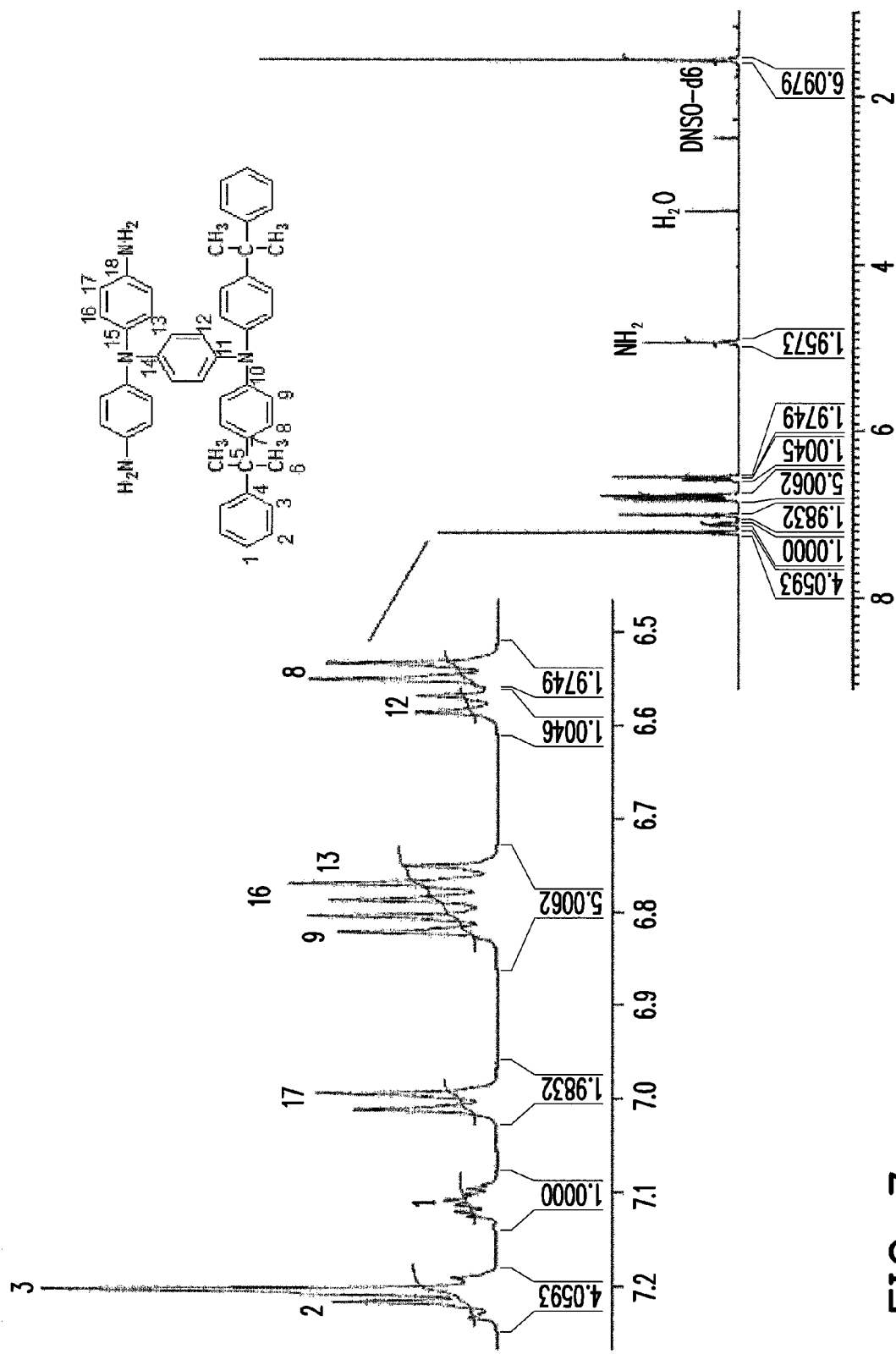
FIGS. 7 and 8 respectively illustrate schematic NMR spectrums of $^1$H-NMR and $^{13}$C-NMR of a BABDPD diamine compound according to an embodiment of the invention.
Figure 8:
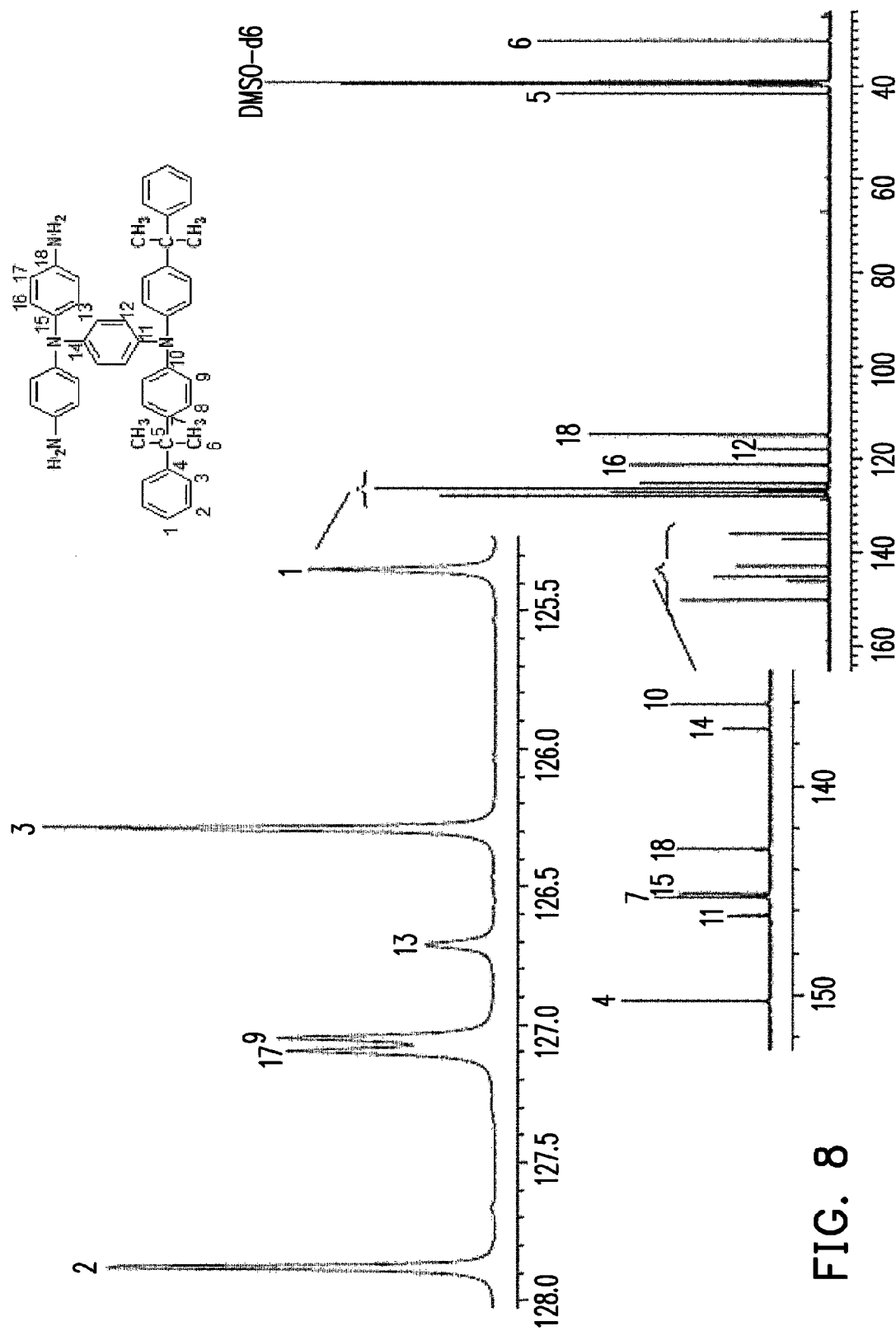

In addition, BABDPD is identified by using the $^1$H-NMR analysis and the $^{13}$C-NMR analysis of the NMR spectrum and the element analysis. FIGS. 7 and 8 respectively illustrate schematic NMR spectrums of $^1$H-NMR and $^{13}$C-NMR of a BABDPD diamine compound according to an embodiment of the invention. In the NMR spectrums shown in FIGS. 7 and 8, s represents a singlet, d represents a doublet, t represents a triplet, q represents a quartet, and m represents a multiplet.

$^1$H NMR (DMSO-d$_6$): δ(ppm)=7.21-7.23 (d, H); 7.19-7.20 (d, 2H); 7.09-7.12 (s, 6H); 6.99-7.01 (d, 2H); 6.80-6.82 (d, 2H); 6.77-6.78 (d, 2H); 6.75-6.77 (d, 1H); 6.56-6.58 (d, 2H); 6.53-6.54 (d, H, He); 4.93 (s, 1H); 1.56 (s, 6H, Hd).

$^{13}$C NMR (DMSO-d$_6$): δ(ppm)=150.2, 146.2, 145.3, 145.2, 143.0, 137.25, 136.0, 127.8, 127.1, 127.0, 126.7, 126.3, 125.3 121.3, 117.8, 114.8, 41.7, 30.4.

The element analysis result of BABDPD of the present embodiment is presented below. Theoretical values are: C, 84.92%; H, 6.83%; N, 8.25%. Analytical values are: C, 84.11%; H, 6.77%; N, 8.17%.

V. Polyimide

A polyimide (PI) of an embodiment of the invention has a structure as shown in Formula (6). The PI is fabricated by performing a polycondensation reaction with BABDPD represented by Formula (4) and a dianhydride compound represented by Formula (5) as monomers.

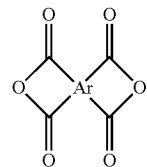

Formula (5)

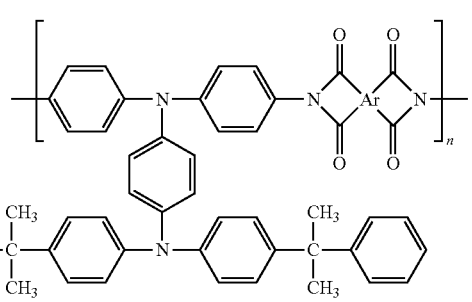

Formula (6)

In Formulae (5) and (6), Ar represents an aromatic group, and n represents a positive integer. Moreover, the new PI is derived from the BABDPD diamine compound as illustrated in Formula (4), and therefore includes bis-triphenylamide.

In one embodiment, Ar in Formulae (5) and (6) is a group illustrated in Formula (5-1), Formula (5-2), Formula (5-3), Formula (5-4), Formula (5-5), or Formula (5-6).

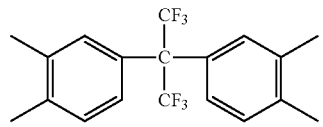

Formula (5-1)

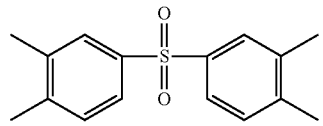

Formula (5-2)

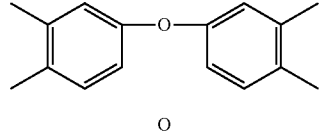

Formula (5-3)

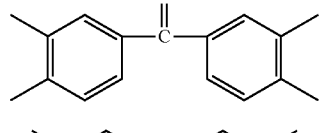

Formula (5-4)

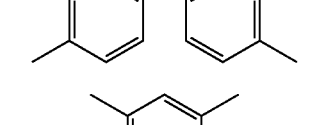

Formula (5-5)

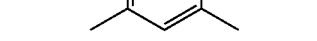

Formula (5-6)

VI. Polyimide Copolymer

The structure of the dianhydride compound has superior thermal properties; that is, the dianhydride compound has high thermal decomposition temperature and high glass transition temperature (Tg). However, the film-forming property thereof has to be improved by other methods.

In one embodiment of the invention, the PI copolymer is fabricated by performing a copolymerization reaction with different molar ratios of the amine compound represented by Formula (4) and at least one dianhydride compound shown in Formula (5) as monomers. The derivatives formed with different ratios of the diamine compound and the at least one dianhydride compound from the copolymerization reaction have superior film-forming property.

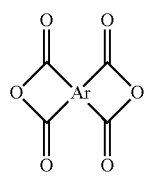

Formula (5)

In Formula (5), Ar represents an aromatic group. In one embodiment, Ar in Formulae (5) and (6) is a group illustrated in Formula (5-1), Formula (5-2), Formula (5-3), Formula (5-4), Formula (5-5), or Formula (5-6).

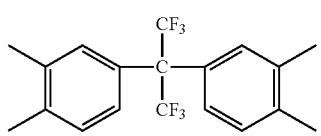

Formula (5-1)

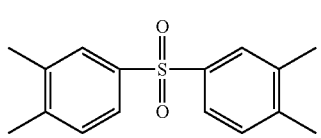

Formula (5-2)

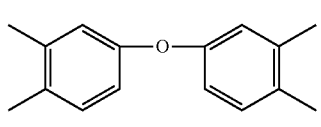

Formula (5-3)

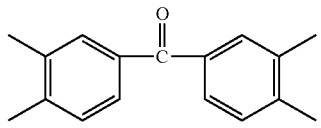

Formula (5-4)

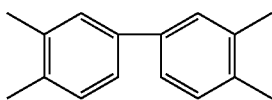

Formula (5-5)

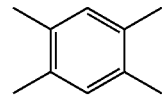

Formula (5-6)

In one embodiment, two different dianhydride compounds are adopted as monomers to synthesize the PI copolymer. Specifically, in Formula (5), two structures of Formulae (5-1) to (5-6) can be selected to stand for Ar in the dianhydride compound, and the dianhydride compounds with different Ar structures are adopted as different monomers. These two dianhydride monomers and the amine compound represented by Formula (4) are then utilized to synthesize the PI copolymer of an embodiment of the invention in a manner of copolymerization. Accordingly, the PI copolymer may have a structure represented by Formula (7). In Formula (7), Ar and Ar' respectively represent aromatic groups different from each other, possibly selected from Formulae (5-1) to (5-6) above; m and n respectively represent positive integers, which can be identical or different.

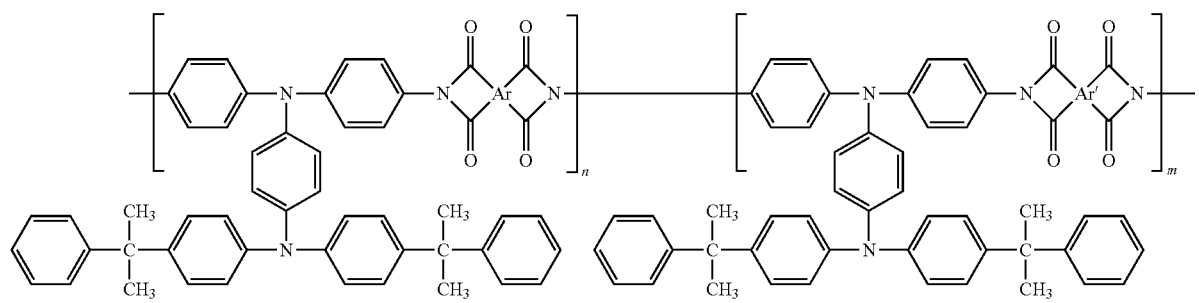

Formula (7)

Next, examples of fabricating the PI and the PI copolymer of the invention are illustrated. In the following, the invention is further illustrated in detail; however, the invention is not limited thereto.

Example 1

Polyimide PI-1

Firstly, 0.883 mmole of BABDPD is dissolved in 3.6 ml of N-methyl-2-pyrrolidinone (NMP) solvent. When the BABDPD has dissolved completely, 0.883 mmol of hexafluoride dianhydride monomer (i.e. Formula (5-1) as Ar group in the dianhydride compound shown in Formula (5)) is then slowly added into the mixture and reacted for 4 hours to obtain a viscous poly amic acid solution. Next, 0.8 ml of acetic anhydride and 0.4 ml of pyridine are added into the poly amic acid solution using cyclization reaction. The reaction mixture is stirred for 1 hour under room temperature. The mixture is then heated to 100° C. and reacted for 3 hours at 100° C. while stirring. After the reaction is completed and the mixture is cooled, the NMP solution is poured into a large amount of methanol for precipitation. The polymer is then washed with methanol and dried in a vacuum environment at 100° C. Finally, the polyimide (PI-1) is obtained.

Example 2

Polyimide PI-3

Firstly, 0.883 mmole of BABDPD is dissolved in 3.6 ml of N-methyl-2-pyrrolidinone (NMP) solvent. When the BABDPD has dissolved completely, 0.883 mmol of ether dianhydride monomer (i.e. Formula (5-3) as Ar group in the dianhydride compound shown in Formula (5)) is then slowly added into the mixture and reacted for 4 hours to obtain a viscous poly amic acid solution. Next, 0.8 ml of acetic anhydride and 0.4 ml of pyridine are added into the poly amic acid solution using cyclization reaction. The reaction mixture is stirred for 1 hour under room temperature. The mixture is then heated to 100° C. and reacted for 3 hours at 100° C. while stirring. After the reaction is completed and the mixture is cooled, the NMP solution is poured into a large amount of methanol for precipitation. The polymer is then washed with methanol and dried in a vacuum environment at 100° C. Finally, the polyimide (PI-3) is obtained.

Example 3

PI copolymer Co-PI (1+5)

Firstly, 0.882 mmole of BABDPD is dissolved in 3.6 ml of N-methyl-2-pyrrolidinone (NMP) solvent. When the BABDPD has dissolved completely, 0.441 mmol of hexafluoride dianhydride monomer (i.e. Formula (5-1) as Ar group in the dianhydride compound shown in Formula (5)) and 0.441 mmol of bi-phenyl dianhydride monomer (i.e. Formula (5-5) as Ar group in the dianhydride compound shown in Formula (5)) are then slowly added into the mixture and reacted for 4 hours to obtain a viscous poly amic acid solution. Next, 0.8 ml of acetic anhydride and 0.4 ml of pyridine are added into the poly amic acid solution using cyclization reaction. The reaction mixture is stirred for 1 hour under room temperature. The mixture is then heated to 100° C. and reacted for 3 hours at 100° C. while stirring. After the reaction is completed and the mixture is cooled, the NMP solution is poured into a large amount of methanol for precipitation. The polymer is then washed with methanol and dried in a vacuum environment at 100° C. Finally, the Co-PI (1+5) is obtained.

Furthermore, identification and a property analysis of a chemical structure of the polyimide PI-1 are illustrated below.

Figure 9:
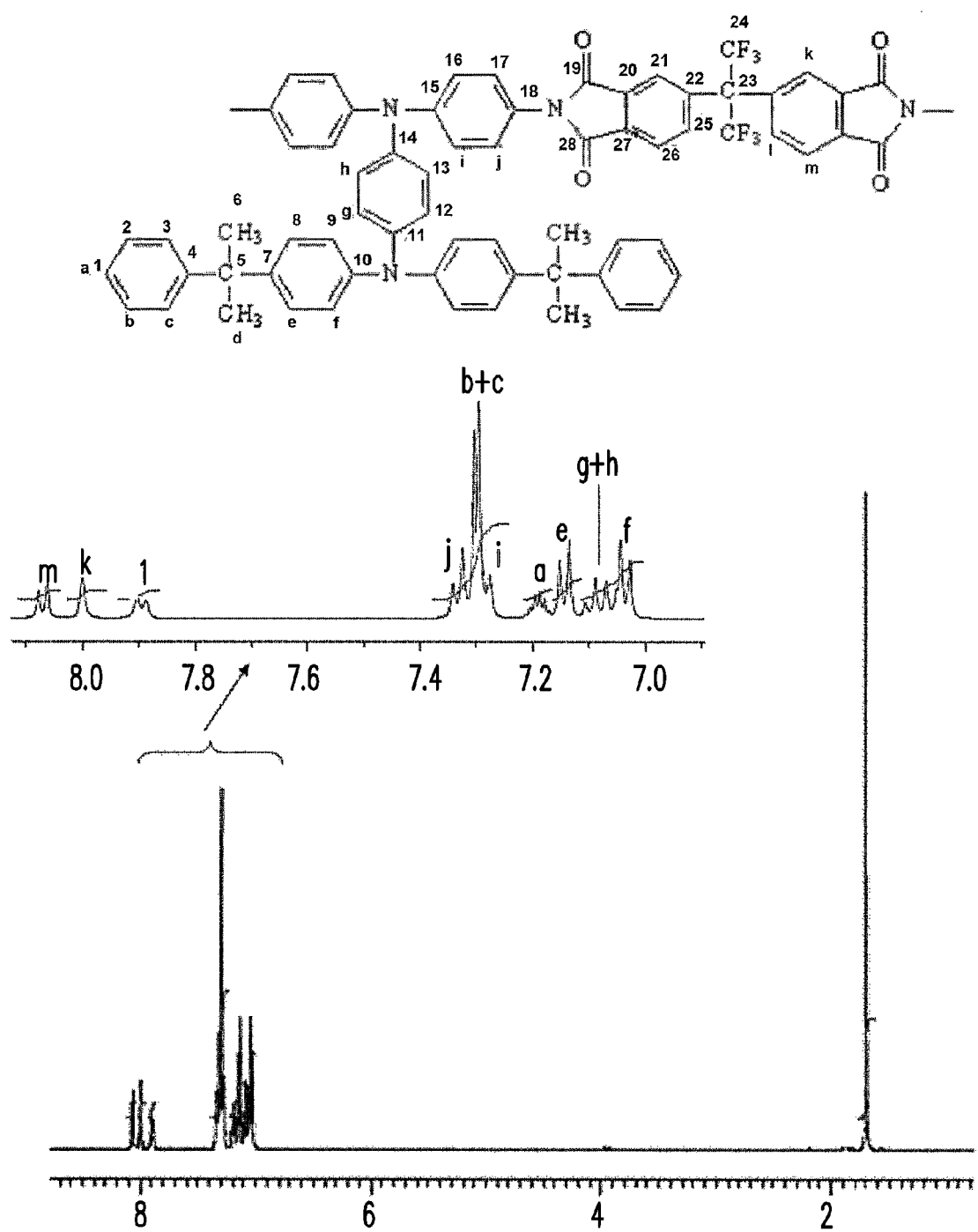
FIG. 9 illustrates schematic NMR spectrum of $^1$H-NMR of polyimide (PI-1) according to an example of the invention.
Figure 10:
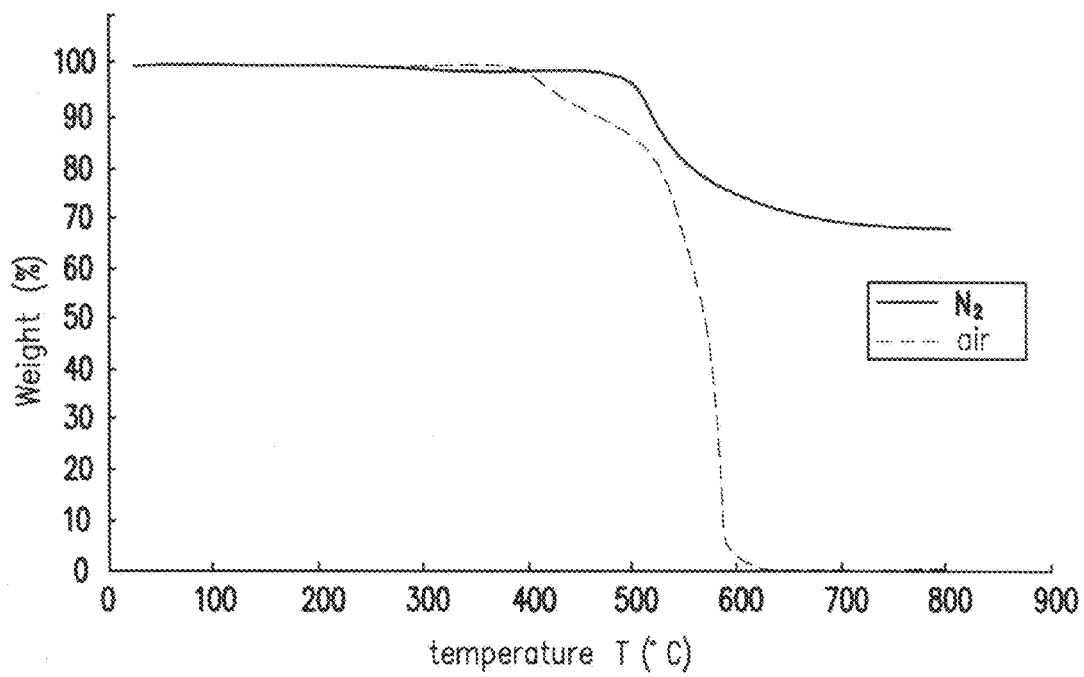
FIG. 10 is a schematic diagram showing a thermogravimetric analysis (TGA) of the polyimide PI-1 in the present example under nitrogen (N2) and under air.

In addition, the polyimide (PI-1) obtained is identified using the $^1$H-NMR analysis of the NMR spectrum. FIG. 9 illustrates schematic NMR spectrum of $^1$H-NMR of polyimide (PI-1) according to an example of the invention. In the NMR spectrum shown in FIG. 9, s represents a singlet, d represents a doublet, t represents a triplet, q represents a quartet, and m represents a multiplet.

$^1$H-NMR (CDCl$_3$): δ 8.05-80; 7 (d, 2H); 7.99 (s, 1H); 7.88-7.90 (d, 1H); 7.32-7.33 (d, 2H); 7.29-7.30 (d, 2H); 7.29 (d, 2H); 7.27 (d, 2H); 7.16-7.20 (m, 1H); 7.14-7.16 (d, 2H); 7.08-7.10 (d, 1H); 7.04-7.06 (d, 1H); 7.02-7.05 (d, 2H); 1.70 (s, 6H).

$^{13}$C NMR (CDCl$_3$): δ(ppm)=166.2, 166.1, 150.6, 147.41, 145.07, 145.02, 144.8, 140.5, 139.0, 135.8, 132.7, 132.4, 127.9, 127.5, 127.3, 127.0, 126.7, 125.5, 125.2, 125.0, 124.5, 124.0, 123.5, 123.2, 42.4, 30.7.

Relative viscosity: the relative viscosity in N,N-dimethylacetamide (DMAc) is 1.2 (a solution concentration of 0.5 g dL$^{-1}$ and a measuring temperature of 30° C.).

Solubility: soluble in solvents such as NMP, pyridine, tetrahydrofuran (THF), DMAc, dimethyl sulfoxide (DMSO), chloroform, cyclohexanone, and so on.

Thin film mechanical property: a tensile strength is 40-54 MPa; an elongation is 2.8-4.2%; a tensile coefficient is 2.2-2.4 GPa.

Figure 11:
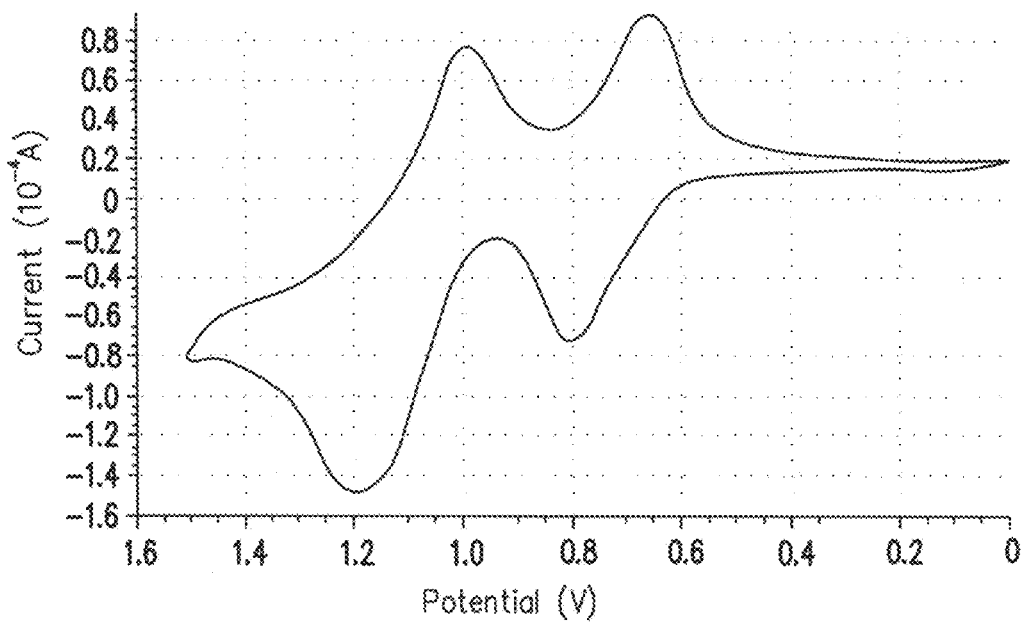
FIG. 11 is a schematic diagram showing a property research result of the polyimide PI-1 in the present example using cyclic voltammetry (CV).

FIG. 11 is a schematic diagram showing a thermogravimetric analysis (TGA) of the polyimide (PI-1) of the present example under nitrogen and under air.

Thermal property: glass transition temperature is higher than 300° C. As shown in FIG. 11, in a TGA measurement in nitrogen, a temperature for 10% decomposition of the polyimide (PI-1) is 528° C.; in a TGA measurement in air, a temperature for 10% decomposition of the polyimide (PI-1) is 466° C.

Figure 12:
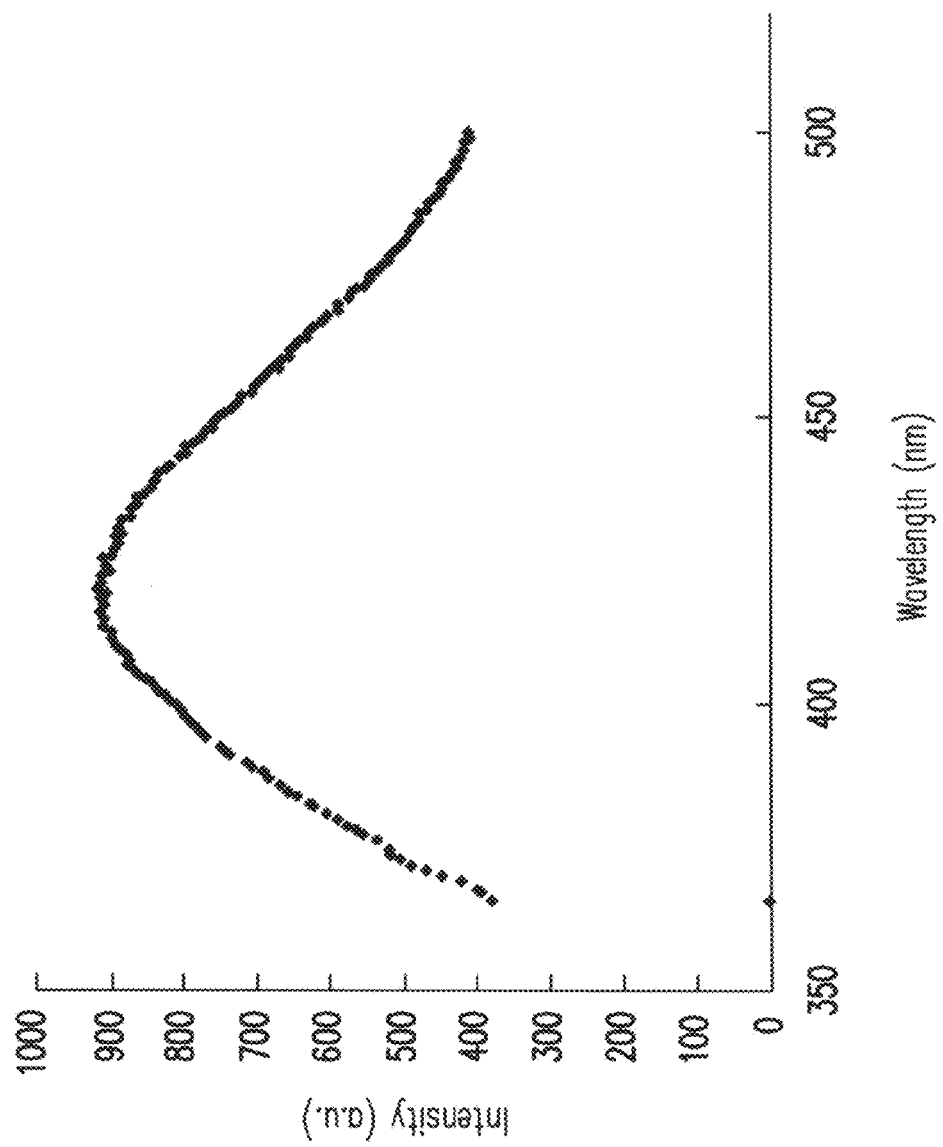
FIG. 12 is a schematic diagram of a luminescent spectrum of phosphorescence excitation of the polyimide PI-1 according to the present example.

FIG. 12 is a schematic diagram showing a property research result of the polyimide PI-1 in the present example using cyclic voltammetry (CV).

The CV diagram in FIG. 12 shows electrochemical properties of the polyimide (PI-1), and the electrochemical properties are illustrated in the following. Electrochemical property: oxidation half potential are respectively 0.73 V and 1.09 V; highest occupied molecular orbital (HOMO)=5.06 eV; lowest unoccupied molecular orbital (LUMO)=1.88 eV; band gap=3.18 eV.

Figure 13:
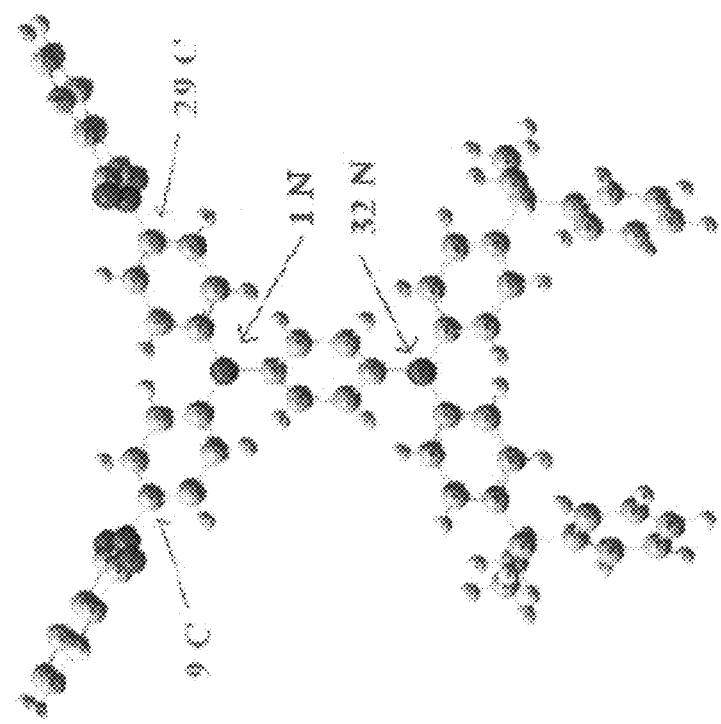
FIGS. 13 and 14 respectively illustrate a structure and electron density distribution contours of a unit polyimide (M1).
Figure 13:
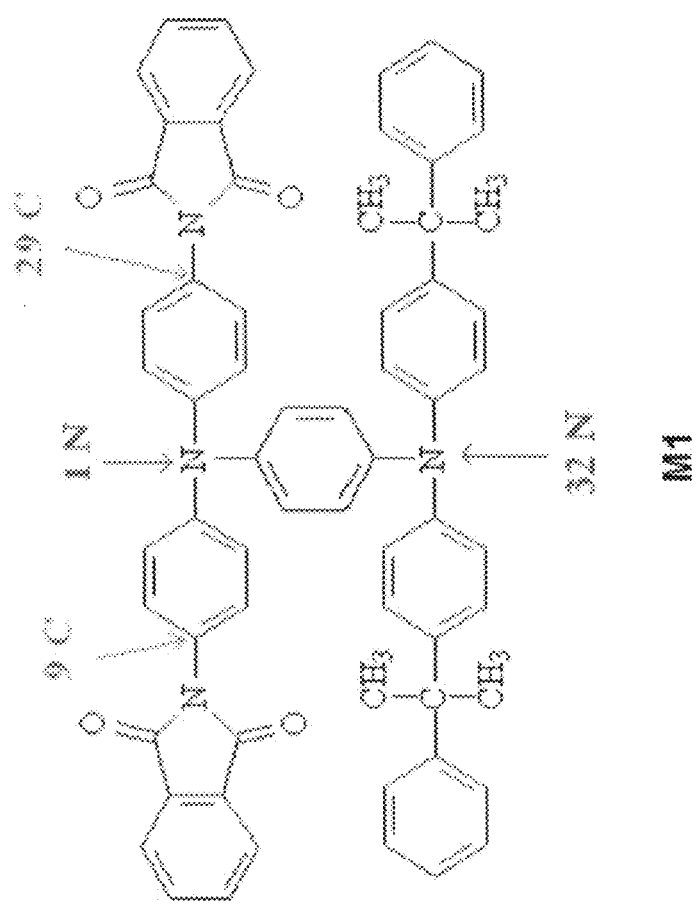

FIG. 13 is a schematic diagram of a luminescent spectrum of phosphorescence excitation of the polyimide (PI-1) according to the present example.

In the present example, a UV-visible light is used to measure a largest absorption wavelength of the polyimide (PI-1). A light of this wavelength is used to excite the polyimide (PI-1), and a result thereof is shown in FIG. 13. Luminescent spectrum of phosphorescence excitation: a largest excitation luminescence wavelength is 437 nm.

Figure 14:
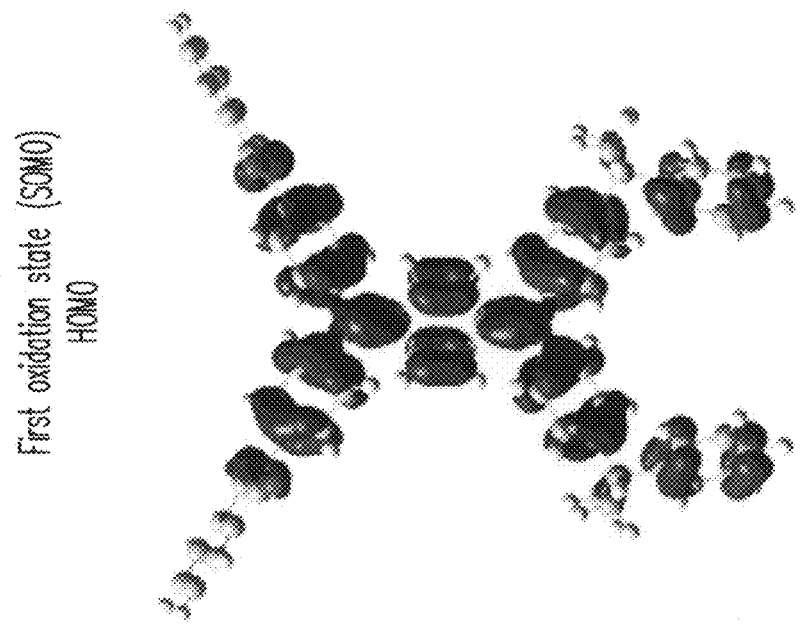
Figure 14:
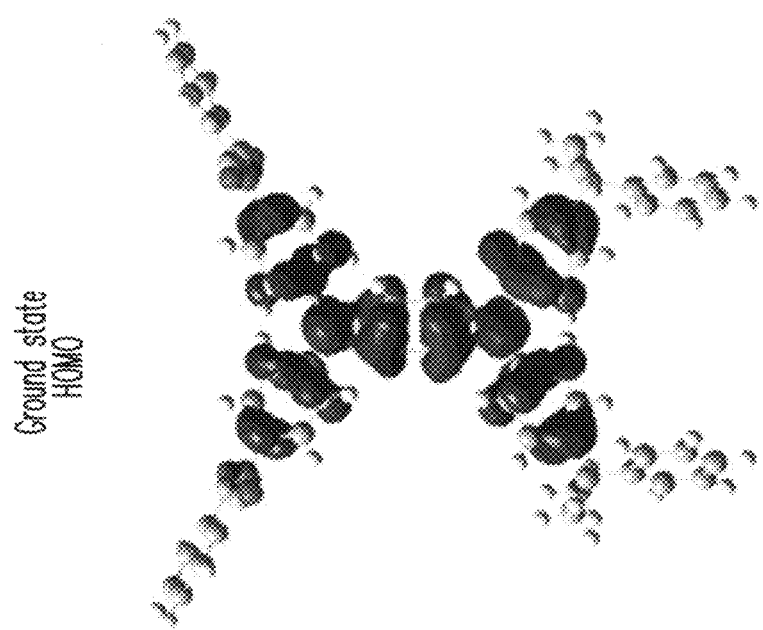
Figure 15:
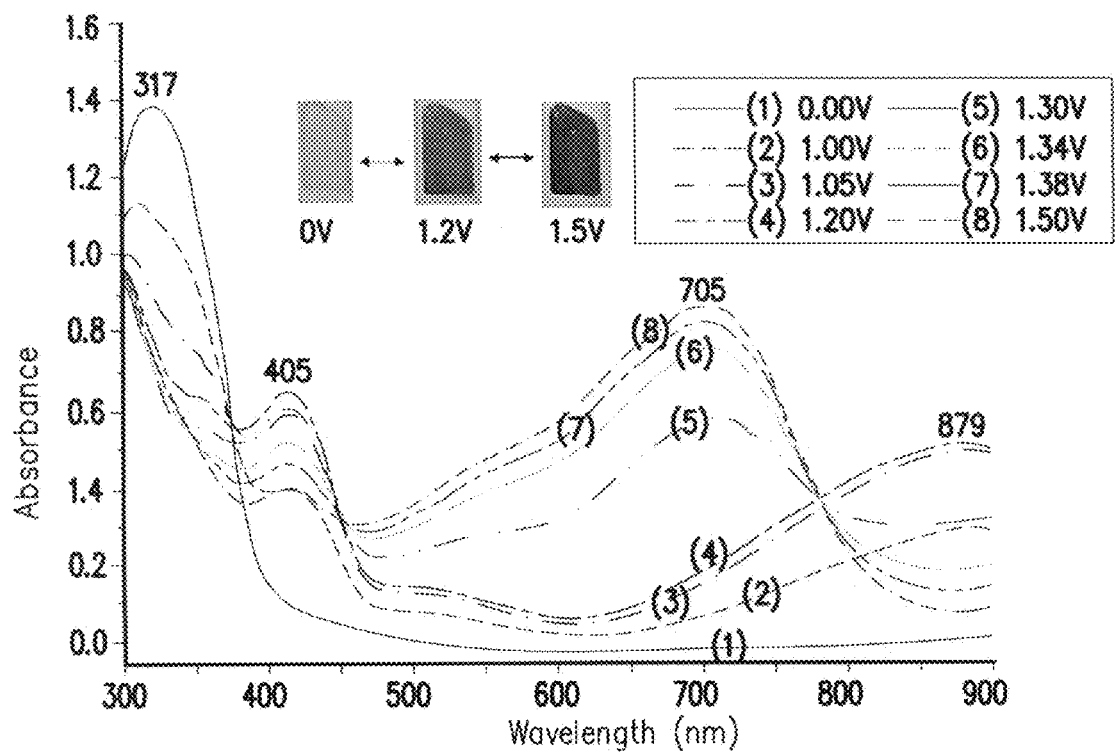
FIG. 15 shows absorption spectrum changes of polyimide (PI-3) in UV-visible light measurement after electrochromism.

FIG. 14 illustrates a structure of a unit polyimide (M1) computed by the Gaussian 03 Software (DFT/B3LYP/6-31G (d)). FIG. 15 shows a ground state and a single occupied molecular orbital (SOMO) electron density distribution contours of a unit polyimide (M1) calculated with the Gaussian 03 Software (DFT/B3LYP/6-31G(d)).

As shown in FIGS. 14 and 15, in the present example, an oxidation mechanism (theoretical calculation) of the polyimide (M1) can be calculated using the Gaussian 03 Software (DFT/B3LYP/6-31G(d). For the first oxidation state (losing the first electron), 1 N, 9 C, 29 C, and 32N atoms respectively contribute 3.6%, 2.0%, 3.8%, and 4.3% of electrons. For the second oxidation state (losing the second electron), 1 N, 9 C, 29 C, and 32 N atoms respectively contribute 2.1%, 1.5%, 1.5%, and 1.6% of electrons. The electron density contours of the ground state and the first oxidation state are included in FIG. 15.

Based on the new oxidation mechanism obtained from the molecular orbital theoretical calculation, it is suggested that the first electron removed from the HOMO of the molecule and the second electron removed from the SOMO of the molecule are not only the lone pair electrons on the nitrogen atom, but are contributed from all of the atoms inside the molecule.

Also, in the identification and property analysis of the chemical structure of the polyimide (PI-3), the solubility, thermal property, and cyclic potential thereof are all similar to those of the polyimide (PI-1).

Figure 16:
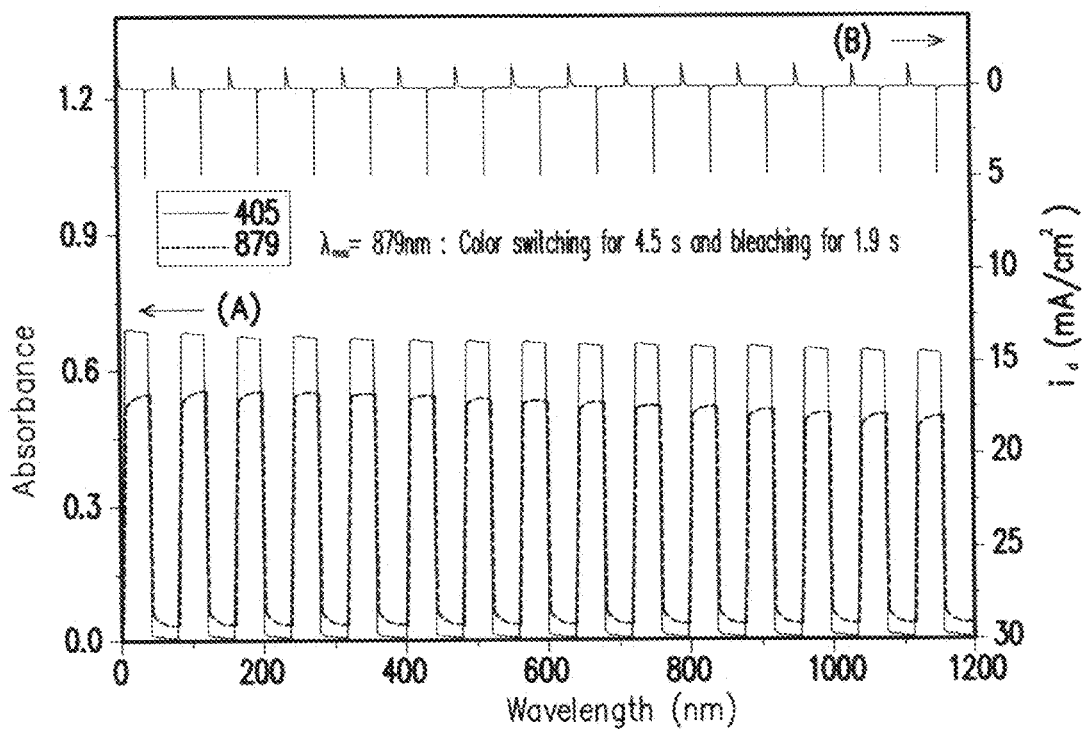
FIG. 16 illustrates (A) a UV-visible light spectrum of the polyimide (PI-3) measured in potential step under a fixed wavelength, and (B) is a current consumption diagram of the polyimide (PI-3) in potential step.

FIG. 16 shows absorption spectrum changes of the polyimide (PI-3) in UV-visible light measurement after electrochromism. In FIG. 16, curve (1) represents 0.00 V, curve (2) represents 1.00 V, curve (3) represents 1.05 V, curve (4) represents 1.20 V, curve (5) represents 1.30 V, curve (6) represents 1.34 V, curve (7) represents 1.38 V, and curve (8) represents 1.50 V.

As illustrated in FIG. 16, in the present example (PI-3), when the potential increases from 0 V to 1.20 V (the first oxidation potential), the absorption of the UV-visible light spectrum at 317 nm decreases gradually, and new absorption peaks are generated at 405 nm and 879 nm. When the potential increases from 1.20 V to 1.50 V (the second oxidation potential), the absorptions of the UV-visible light spectrum at 405 nm and 879 nm decrease gradually, and a new peak is generated at 705 nm. At the same time, the polyimide (PI-3) thin film changes from pale yellow into green as the potential increases from 0 V to 1.20 V (the first oxidation potential). Later, the polyimide (PI-1) thin film turns into blue as the potential increases to 1.50 V (the second oxidation potential).

FIG. 17 illustrates (A) a UV-visible light spectrum of the polyimide (PI-3) measured in potential step under a fixed wavelength, and (B) is a current consumption diagram of the polyimide (PI-3) in potential step.

In the present example, an electrochromic switching time of the polyimide (PI-3) is calculated from the UV-visible light spectrum measured in the potential step at a fixed wavelength (as shown in FIG. 17). Here, the electrochromic switching time is defined as the time attaining 90% of the intensity variation of the absorption spectrum. The polyimide (PI-3) thin film in the present example under the UV-visible light with the fixed $\lambda_{max}$=879 nm has an electrochromic switching time (color switching) of 4.5 second (s) (oxidation), while the reduction time (color bleaching) is only 1.9 s. This reveals that the rates of oxidation and reduction of PI-3 are not the same.

Furthermore, identification and a property analysis of a chemical structure of the Co-PI (1+5) are illustrated below.

Relative viscosity: the relative viscosity in DMAc is 1.0 (a solution concentration of 0.5 g dL$^{-1}$ and a measuring temperature of 30° C.).

Solubility: soluble in solvents such as NMP, pyridine, tetrahydrofuran (THF), DMAc, dimethyl sulfoxide (DMSO), chloroform, cyclohexanone, and so on.

Thermal property: glass transition temperature is higher than 280° C.; 10% decomposition temperature is higher than 450° C. in nitrogen; 10% decomposition temperature is higher than 400° C. in air.

Thin film mechanical property: a tensile strength is 64.0 MPa; an elongation is 7%; a tensile coefficient is 2.1 GPa.

The PI and the PI copolymer (Co-PI) are fabricated by performing a polycondensation or a copolymerization with the diamine compound and the commercially manufactured or self-synthesized dianhydride compounds as monomers. The new PI and Co-PI contain imide groups, which can be categorized into rigid aromatic groups and triphenylamide groups. When the compound contains more benzene rings, the features of heat-resistance, water-resistance, chemical-resistance, rubbing resistance, and hydrophobicity of the polymer are enhanced, and the polymer has a higher glass transition temperature as well. Hence, the new PI and Co-PI can be adopted as alignment films for optical-electronic displays, thereby enhancing the performance of electronic products.

It should be noted that since the PI and the Co-PI of the invention includes a bis-triphenylamide group, the PI and the Co-PI therefore has superior solubility, high glass transition temperature and high thermal stability. Furthermore, the polyimide possesses electrochemical properties and electrochromic properties. In details, the new PI and the Co-PI each containing bis-triphenylamide in the invention have high carrier mobility, low ionization potential, and a feature of forming thin films easily. In addition, the nitrogen atom at the center of the PI and the Co-PI each containing bis-triphenylamide has an oxidation-reduction (redox) ability and can therefore be applied in electrochromic material. As a consequence, the PI and the Co-PI can be widely utilized in constructions of mirrors, indicators, electrochromic displays, smart windows, and so on.

Moreover, in the new PI and the Co-PI each containing bis-triphenylamide, the nitrogen atom at the center is easily oxidized such that electrons are lost. The PI and the Co-PI can be thus used as superior hole-transporting materials. Hence, the PI and the Co-PI containing bis-triphenylamide can also fabricate thin layers of hole-transporting material, so as to be applied in organic light emitting diodes (OLED), solar cells, photoreceptors, emitters, electro-luminescent elements, and so on.

In summary, the nitro compound, the amine compound, and the PI and the Co-PI derived therefrom at least have a part or all of the advantages listed below:

1. The nitro compound, the amine compound, and the PI and the Co-PI derived therefrom each includes a triphenylamide group. Therefore, the PI and the Co-PI each containing bis-triphenylamide have superior solubility, high glass transition temperature, and thermal stability. The PI and the Co-PI can be processed easily and has a wide application scope.

2. The nitro compound, the amine compound, and the PI and the Co-PI derived therefrom can provide properties required by the elements according to the application scope thereof. The PI and the Co-PI each containing bis-triphenylamide have electrochemical properties and can be applied in electrochemical materials.

Although the invention has been described with reference to the above embodiments, it will be apparent to one of the ordinary skill in the art that modifications to the described embodiment may be made without departing from the spirit of the invention. Accordingly, the scope of the invention will be defined by the attached claims not by the above detailed descriptions.

What is claimed is:

1. A polyimide, fabricated by performing a polycondensation reaction using the amine compound of Formula (4) and a dianhydride compound shown in Formula (5) as monomers, and represented by Formula (6):

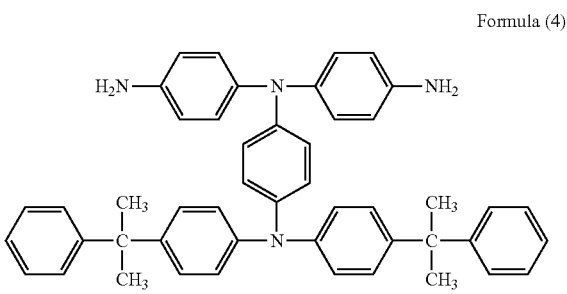 [SMILES: CC(C)(c1ccccc1)c1ccc(N(c2ccc(N(c3ccc(N)cc3)c3ccc(N)cc3)cc2)c2ccc(C(C)(C)c3ccccc3)cc2)cc1]

Formula (4)

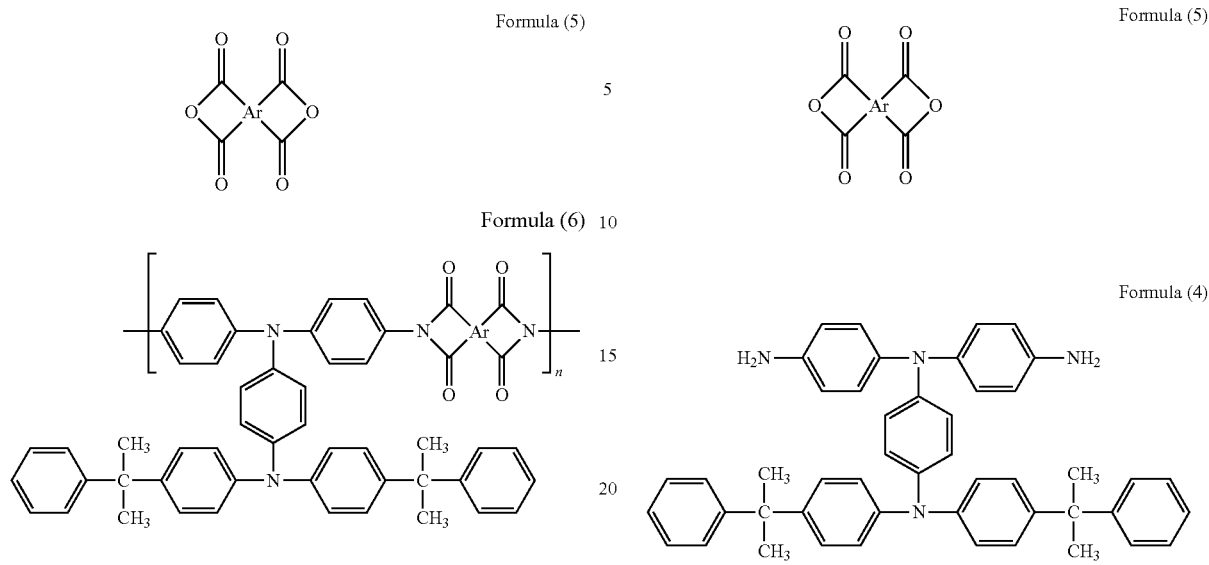

wherein in Formula (5) and Formula (6), Ar represents an aromatic group, and n represents a positive integer.

2. The polyimide as claimed in claim 1, wherein in Formula (5) and Formula (6), Ar represents a group selected from Formula (5-1) to Formula (5-6)

wherein in Formula (5), Ar represents an aromatic group.

4. The polyimide copolymer as claimed in claim 3, wherein in Formula (5), Ar represents a group selected from Formula (5-1) to Formula (5-6)

3. A polyimide copolymer, fabricated by performing a copolymerization reaction of the amine compound of Formula (4) and at least one dianhydride compound shown in Formula (5) as monomers:

5. The polyimide copolymer as claimed in claim 3, wherein the at least one dianhydride compound adopted as monomers comprises two different dianhydride compounds, and the polyimide copolymer is represented by Formula (7):

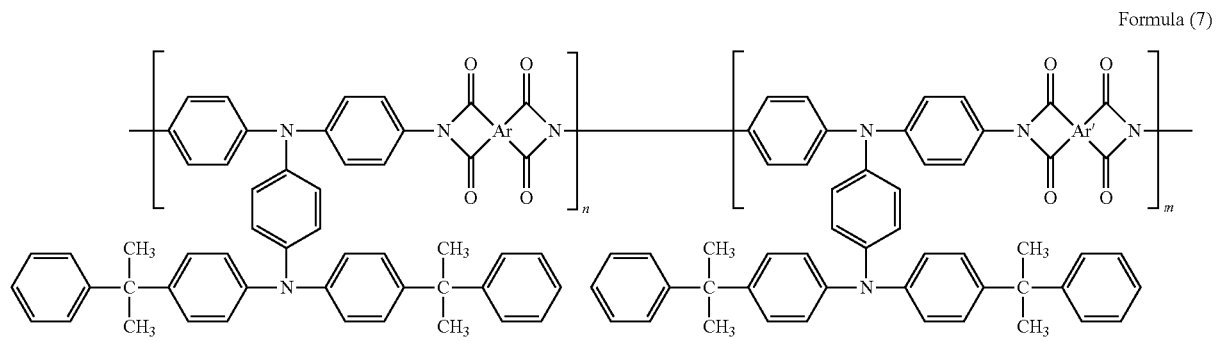

Formula (7)

wherein in Formula (7), Ar and Ar' respectively represent aromatic groups that are different from each other, and m and n respectively represent positive integers.

6. The polyimide copolymer as claimed in claim 5, wherein in Formula (7), Ar and Ar' respectively represent two groups selected from Formula (5-1) to Formula (5-6)

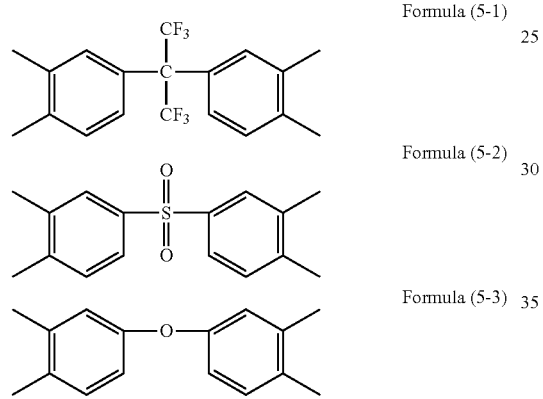

Formula (5-1)

Formula (5-2)

Formula (5-3)

-continued

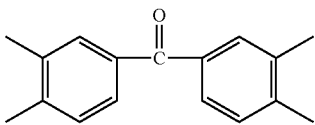

Formula (5-4)

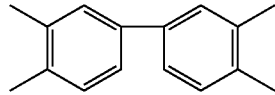

Formula (5-5)

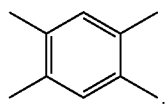

Formula (5-6)

\* \* \* \* \*